(12) United States Patent
Chen et al.

(10) Patent No.: US 10,847,278 B2
(45) Date of Patent: Nov. 24, 2020

(54) MULTIFUNCTIONAL NANOPARTICLES

(71) Applicant: MASSACHUSETTS INSTITUTE OF TECHNOLOGY, Cambridge, MA (US)

(72) Inventors: Ou Chen, Somerville, MA (US); Moungi G. Bawendi, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 16/283,750

(22) Filed: Feb. 23, 2019

(65) Prior Publication Data

US 2019/0244721 A1    Aug. 8, 2019

Related U.S. Application Data

(62) Division of application No. 13/852,091, filed on Mar. 28, 2013, now Pat. No. 10,217,540.

(60) Provisional application No. 61/616,663, filed on Mar. 28, 2012.

(51) Int. Cl.
*H01B 1/00* (2006.01)
*G01N 33/50* (2006.01)
*A61K 49/18* (2006.01)
*A61K 49/00* (2006.01)

(52) U.S. Cl.
CPC ........... *H01B 1/00* (2013.01); *A61K 49/0093* (2013.01); *A61K 49/1818* (2013.01); *G01N 33/5005* (2013.01); *Y10T 428/2982* (2015.01); *Y10T 428/2993* (2015.01)

(58) Field of Classification Search
CPC .. H01B 1/00; A61K 49/0093; A61K 49/1818; G01N 33/5005; Y10T 428/2993; Y10T 428/2982
See application file for complete search history.

(56) References Cited

U.S. PATENT DOCUMENTS

| 7,563,457 | B2 | 7/2009 | Cha et al. |
| 8,435,496 | B2 | 5/2013 | Brougham et al. |
| 2010/0104514 | A1 | 4/2010 | Brougham et al. |
| 2012/0055860 | A1 | 3/2012 | Wyndham |
| 2012/0059240 | A1 | 3/2012 | Sailor et al. |
| 2013/0023714 | A1 | 1/2013 | Johnston et al. |

FOREIGN PATENT DOCUMENTS

WO    2010048623    4/2010

OTHER PUBLICATIONS

International Preliminary Report on Patentability for PCT/US2013/034241 dated Oct. 1, 2014.
International Search Report and Written Opinion of the International Searching Authority dated Jun. 17, 2013 for PCT/US2013/034241.

*Primary Examiner* — Robert S Cabral
(74) *Attorney, Agent, or Firm* — Honigman LLP

(57) ABSTRACT

Multifunctional nanoparticles can include two or more different populations of nanocrystals that impart a combination of properties arising from the constituent populations in a single, multifunctional nanoparticle.

19 Claims, 13 Drawing Sheets

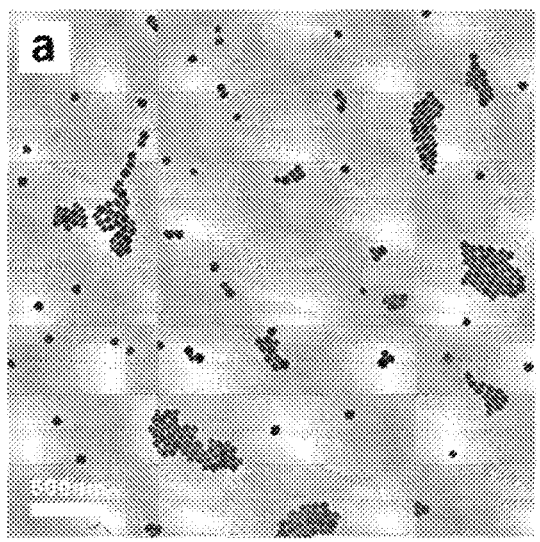
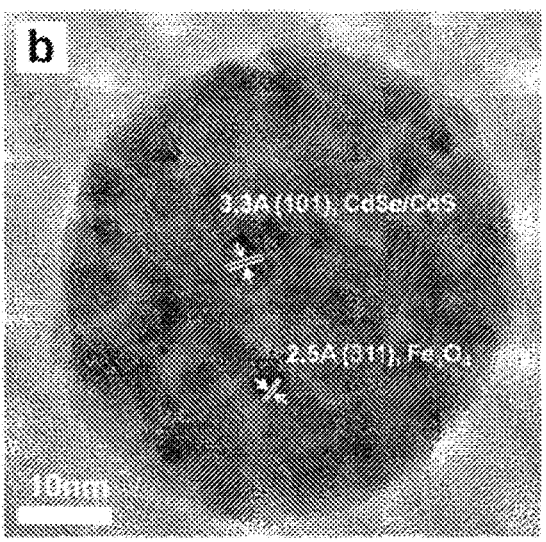
FIG. 3a  FIG. 3b
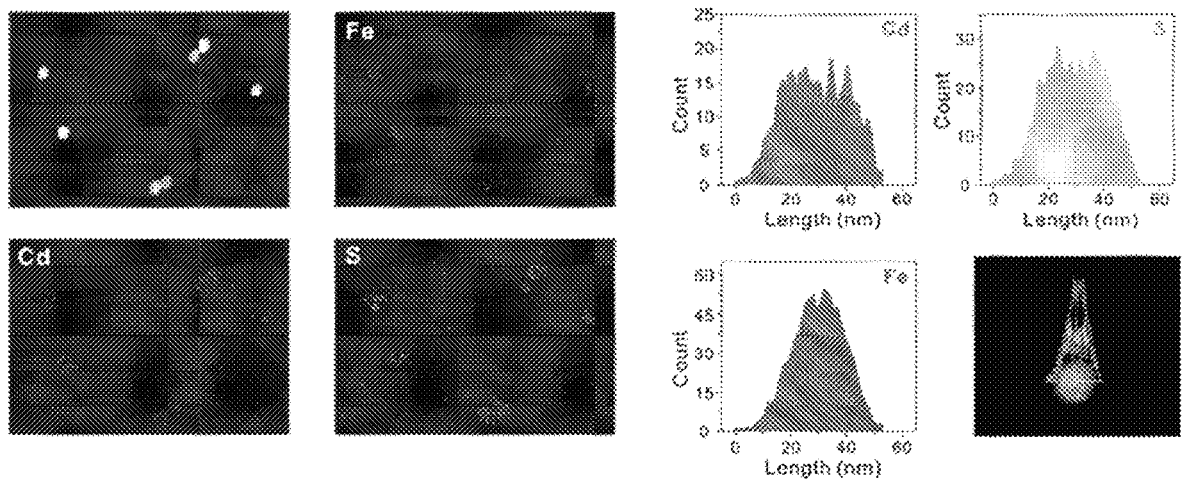
FIG. 4

MULTIFUNCTIONAL NANOPARTICLES

CLAIM OF PRIORITY

This application is a divisional of U.S. Application No. 13/852,091, filed Mar. 28, 2013, now U.S. Pat. No. 10,217,540, which claims priority to U.S. Provisional Application No. 61/616,663, filed Mar. 28, 2012, each of which is incorporated by reference in its entirety.

FEDERALLY SPONSORED RESEARCH OR DEVELOPMENT

This invention was made with government support under Grant No. R01 CA126642 awarded by the National Institutes of Health. The government has certain rights in this invention.

TECHNICAL FIELD

This invention relates to multifunctional nanoparticles and methods of making and using them.

BACKGROUND

Nanoparticles can provide a wide variety of desirable properties, among them light emission, magnetism, and electrical conductivity or semiconductivity. However, combinations of these properties can be difficult to achieve in a single nanoparticle. For example, semiconductor nanocrystals can provide narrow band light emission at selected wavelengths spanning the visible and IR spectrum. However, a single nanocrystal emits at only one wavelength; and, typically, such semiconductor nanocrystals are nonmagnetic. There is a need for multifunctional nanoparticles that can combine one or more constituent nanoparticles (and their advantageous properties) in a single nanoparticle.

SUMMARY

Uniform multifunction nanoparticles having a narrow size distribution can be prepared by a simple method. The multifunctional nanoparticles include nanoparticles from two or more starting populations of nanoparticles which have different properties that may not be available in a single starting population of nanoparticles. For example, a magneto-fluorescent nanoparticle can include both highly luminescent semiconductor nanocrystals which emit light at a desired wavelength, and magnetic nanoparticles; or a multicolor nanoparticle can include semiconductor nanocrystals that emit light at two or more desired wavelengths. The multifunctional nanoparticles can be overcoated with a thin, optically transparent silica shell to facilitate further functionalization, reduce toxicity, and increase water solubility.

In one aspect, a multifunctional nanoparticle includes a first population of nanoparticles and an assembly polymer associated with the first population of nanoparticles. The multifunctional nanoparticle can further include a second population of nanoparticles distinct from the first population, where the assembly polymer is associated with the first and second populations of nanocrystals.

The multifunctional nanoparticle can have a diameter no greater than 1,000 nm, no greater than 500 nm, or no greater than 100 nm. In some cases, the first population can have an average diameter no greater than 50 nm, and the second population can have an average diameter no greater than 50 nm.

The assembly polymer can be non-covalently associated with the first and second populations. The multifunctional nanoparticle can further include a shell including a silicon oxide on a surface of the multifunctional nanoparticle. The shell including a silicon oxide can be further functionalized. The shell including a silicon oxide can be further functionalized with a dye, a polymer, a biomolecule, or a member of a binding pair.

The first population can be a population of semiconductor nanocrystals. The second population can be a population of semiconductor nanocrystals, magnetic nanoparticles, metal nanoparticles, carbon-based nanoparticles, polymer nanoparticles, or ceramic nanoparticles. In some cases, the first population can be a population of semiconductor nanocrystals and the second population can be a population of semiconductor nanocrystals or a population of magnetic nanoparticles.

The first population can be preferentially located toward the center of the multifunctional nanoparticle. The second population can be preferentially located toward the periphery of the multifunctional nanoparticle.

In another aspect, a method of making a multifunctional nanoparticle includes forming a mixture including a first solvent, a second solvent which is substantially immiscible with the first solvent, a first population of nanoparticles, and a surfactant; removing at least a portion of the first solvent from the mixture; and adding an assembly polymer to the mixture, thereby associating the assembly polymer with the first population of nanoparticles to form a multifunctional nanoparticle including the first population of nanoparticles and the assembly polymer.

The mixture can further include a second population of nanoparticles, and the multifunctional nanoparticle can further include the second population of nanoparticles. Adding an assembly polymer can include contacting the mixture with a composition including the assembly polymer and a third solvent. The method can further include isolating the multifunctional nanoparticles from the mixture. The assembly polymer can be selected to non-covalently associate with the first and second populations.

The method can further include forming a shell including a silicon oxide on a surface of the multifunctional nanoparticle. The method can further include functionalizing the shell including a silicon oxide. Functionalizing the shell including a silicon oxide can include covalently linking a dye, a polymer, a biomolecule, or a member of a binding pair to the metal oxide shell.

The first population can be a population of semiconductor nanocrystals. The second population can be a population of semiconductor nanocrystals, magnetic nanoparticles, metal nanoparticles, carbon-based nanoparticles, polymer nanoparticles, or ceramic nanoparticles.

In the method, the multifunctional nanoparticle can have a diameter no greater than 1,000 nm, no greater than 500 nm, or no greater than 100 nm. In some cases, the first population can have an average diameter no greater than 50 nm, and the second population can have an average diameter no greater than 50 nm.

In another aspect, a method of studying a living organism can include adding a multifunctional nanoparticle into the living organism, wherein the multifunctional nanoparticle includes a first population of nanoparticles and an assembly polymer associated with the first population of nanoparticles. In certain embodiments, the living organism can be a cell. In certain embodiments, the living organism can be a mouse.

A magnetic field can be applied to the multifunctional nanoparticle. The multifunctional nanoparticle can be both magnetic and photoluminescent. The multifunctional nanoparticle can include magnetic constituent nanoparticles and photoluminescent constituent nanoparticles.

Other aspects, embodiments, and features will be apparent from the following description, the drawings, and the claims.

BRIEF DESCRIPTION OF THE DRAWINGS

FIGS. 3a-3b are TEM images of nanocrystal-$Fe_3O_4$ magneto-fluorescent multifunctional nanoparticles.

FIG. 4 shows elemental mapping (left) and line-scanning (right) results for nanocrystal-$Fe_3O_4$ magneto-fluorescent multifunctional nanoparticles.

DETAILED DESCRIPTION

Figure 1:
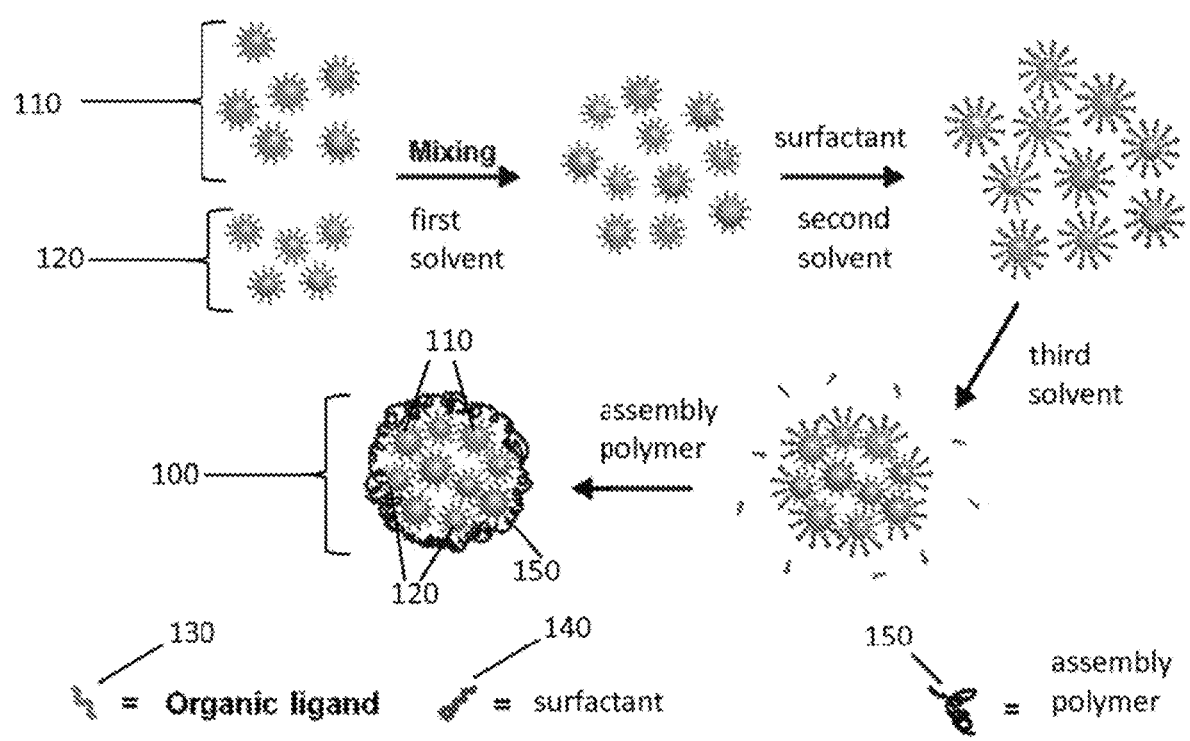
FIG. 1 is a schematic depiction of multifunctional nanoparticles and a method of preparing them.

Referring to FIG. 1, multifunctional nanoparticle 100 includes a first population of nanoparticles 110, an optional second population of nanoparticles 120, and an assembly polymer 150. An assembly polymer is a material that helps constituent nanoparticles 110, and optionally nanoparticles 120, form a multifunctional nanoparticle. Constituent nanoparticles can be magnetic nanoparticles, where the nanoparticles comprise a magnetic material. Constituent nanoparticles can be photoluminescent nanoparticles, including but not limited to semiconductor nanocrystals. Multifunctional nanoparticle 100 can optionally include one or more additional populations of nanoparticles (not shown in FIG. 1). Multifunctional nanoparticle 100 can also include additional polymers or other components as desired. Advantageously, multifunctional nanoparticle 100 can bring together diverse properties of different populations of nanoparticles (i.e., properties of populations 110 and 120) in a single nanoparticle. In particular, multifunctional nanoparticle can have a combination of properties that is not otherwise available in a single nanoparticle. As but one example, multifunctional nanoparticle 100 can include a population of non-magnetic, photoluminescent nanoparticles and a population of magnetic but non-photoluminescent nanoparticles to provide a multifunctional nanoparticle which is both magnetic and photoluminescent.

Population 110 includes nanoparticles which can bear organic ligands on an outer surface of each of the nanoparticles in population 110. Similarly, population 120 includes nanoparticles which can bear organic ligands on an outer surface of each of the nanoparticles in population 120. The ligands of population 110 can be the same as or different from the ligands in population 120. Preferably, the ligands of both populations are substantially hydrophobic and are selected such that populations 110 and 120 can be dispersed in a common solvent. For example, the ligands of populations 110 and 120 can each include a hydrophobic alkyl group (e.g. a $C_6$ or longer branched or unbranched alkyl chain) such that populations 110 and 120 can each be dispersed in a hydrophobic solvent such as chloroform. In some embodiments, one or both of populations 110 and 120 can omit organic ligands, provided that populations 110 and 120 can be dispersed in a common solvent.

In making multifunctional nanoparticle 100, first population 110 and second population 120 are each dispersed in a common first solvent, combined and mixed. When the multifunctional nanoparticle is to include only a first population of nanoparticles, the first population is dispersed in a solvent. The mixed populations are then exposed to a solution including a second solvent and a surfactant, to make a mixed-solvent composition (e.g., an emulsion). The first and second solvents are poorly miscible, substantially immiscible, or immiscible. The surfactant facilitates transfer of populations 110 and 120 from the first solvent phase to the second solvent phase. In one example, the first solvent is a hydrophobic organic solvent (e.g., chloroform) and the second solvent is water. The first solvent is removed from the mixed-solvent composition (e.g., by evaporation).

After the first solvent has been removed, a third solvent and assembly polymer (e.g., a solution of the assembly polymer in the third solvent) are combined with the nanoparticle mixture. The mixture can be agitated to insure thorough mixing. The third solvent can help disperse the organic ligands from the surfaces of the nanoparticles, encouraging the nanoparticles to interact with one another and the assembly polymer to interact with the nanoparticles (e.g., with the organic ligands on the surfaces of the nanoparticles of populations 110 and 120) so as to associate nanoparticles of first population 110, nanoparticles of second population 120, and the assembly polymer. The association can be non-covalent or covalent; preferably the association is a non-covalent association. A non-covalent association can involve one or more intermolecular interactions including but not limited to hydrogen bonds, hydrophobic interactions, electrostatic interactions, van der Waals forces, or pi-pi interactions.

After the assembly polymer has been added and multifunctional nanoparticles have formed, the multifunctional nanoparticles can be isolated from the mixture, for example by centrifugation. Once isolated, the multifunctional nanoparticles can be dispersed in a solvent Depending on factors such as the chemical nature of the nanoparticles, organic ligands, assembly polymer, and other components of the multifunctional nanoparticle, the multifunctional nanoparticle can be dispersed in a desired solvent. For example, the multifunctional nanoparticle can be dispersed in, e.g., an aqueous solvent, an alcohol, or a mixed solvent.

One or both of populations 110 and 120 can have a narrow size distribution, e.g., can be a monodisperse population of nanoparticles. The nanoparticles of populations 110 and 120 can, individually, be a sphere, rod, wire, disk, or other shape. Suitable nanoparticles include but are not limited to semiconductor nanocrystals, magnetic nanoparticles, metal nanoparticles (e.g., gold nanoparticles and silver nanoparticles), carbon-based nanoparticles (such as fullerenes and carbon nanotubes), polymer nanoparticles, ceramic nanoparticles (e.g., metal oxide nanoparticles such as silica nanoparticles, titanium dioxide nanoparticles, and zinc oxide nanoparticles), or other nanoparticulate materials.

Desirable properties of nanoparticles that can be selected for inclusion in an multifunctional nanoparticle include, but are not limited to, optical properties such as absorption at a desired wavelength, absorption in a narrow spectral range, photoluminescence at a desired wavelength, or photoluminescence in a narrow spectral range; magnetic properties such as paramagnetism or superparamagentism; catalytic properties; binding affinity for a desired binding partner (e.g., when a population of nanoparticles is modified with a member of a specific binding pair); electrical properties such as conductivity, semiconductivity, or facilitation of charge separation; or any other desirable property of a nanoparticle. In some embodiments, a multifunctional nanoparticle can include two or more populations of nanocrystals that photoluminescence at different desired wavelengths. In some embodiments, a multifunctional nanoparticle can include a population of nanoparticles that photoluminescence at a desired wavelength, and a population of magnetic nanoparticles.

Figure 2:
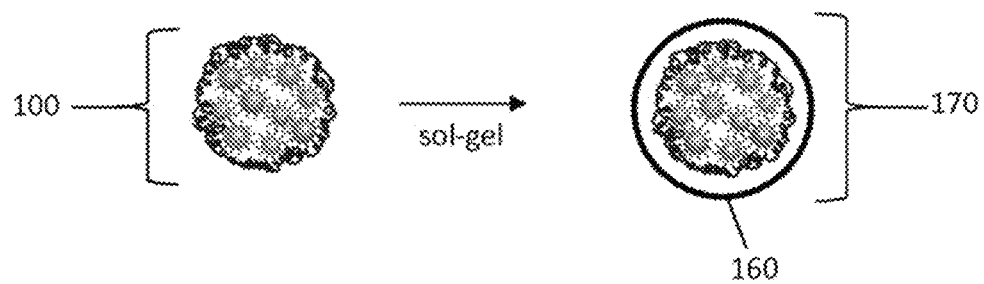
FIG. 2 is a schematic depiction of metal oxide coated multifunctional nanoparticles and a method of preparing them.

FIG. 2 illustrates a multifunctional nanoparticle 100 including a metal oxide shell 160 on a surface of multifunctional nanoparticle 100. In some cases, the metal oxide shell can substantially coat the surface of multifunctional nanoparticle 100 or substantially encapsulate multifunctional nanoparticle 100. Metal oxide shell 160 can be added to multifunctional nanoparticle 100 by carrying out a sol-gel process in the presence of multifunctional nanoparticle 100, thus providing metal-oxide coated multifunctional nanoparticle 170. A metal oxide coating can stabilize and protect multifunctional nanoparticle 100, and provide additional opportunities for functionalization. The metal oxide can include, for example, a silicon oxide, a titanium oxide, or a mixture thereof; these can be readily prepared by a sol-gel process. Other metal oxides can be used.

In particular, a metal oxide coated multifunctional nanoparticle can be functionalized using reagents bearing a desired functional group. For example, a silica coated multifunctional nanoparticle can be functionalized using a silane or siloxane reagent bearing a functional group. Suitable functional groups can include, for example, polymers (e.g., a poly(ethylene glycol)), reactive groups (e.g., amines, thiols, or carboxylic acids), biomolecules (including, e.g., proteins, carbohydrates, nucleic acids, lipids, hormones, and metabolites), or members of binding pairs. A binding pair means a pair of molecules capable of specific binding to one another. One common example of a binding pair is biotin/avidin; complementary nucleic acid sequences (e.g., complementary oligonucleotides) are also examples of binding pairs. Any suitable binding pair may be used.

In some cases, the metal oxide is functionalized with a reactive group that can be further functionalized. This approach can be desirable when the ultimate desired functional group (e.g., a biomolecule) is not suitable for direct reaction with a metal oxide. In one example, a silica-coated multifunctional nanoparticle can be functionalized with amino groups, using a reagent such as 3-(aminopropyl) trimethoxysilane. The amino groups can be reacted with a wide variety of functional groups, including but not limited to a dye, a polymer, a biomolecule, or a member of a binding pair. One common scheme for modifying amino groups in aqueous environments is to react the amine with an N-hydroxy succinimidyl ester, which are readily prepared from a compound having carboxylic acid moieties. Biomolecules in particular are suitable for being linked to amine groups in this manner.

The size of the multifunctional nanoparticle depends upon factors including the size and number of constituent nanoparticles present in the multifunctional nanoparticle, the nature of the ligands on the constituent nanoparticles, the nature of the assembly polymer (including molecular weight), and the nature of any other components in the multifunctional nanoparticle. For example, when the multifunctional nanoparticles are prepared in the presence of amphiphilic compounds such as oleic acid and/or oleyl amine, the size of the final multifunctional nanoparticles can be controlled by selecting appropriate compounds in appropriate concentrations.

An individual multifunctional nanoparticle can have a diameter in the range of 10 nm to 1,000 nm, or greater. A population of multifunctional nanoparticles can have an average diameter in the range of 10 nm to 1,000 nm, or greater. In some cases, a multifunctional nanoparticles can have an average diameter of no greater than 1,000 nm, 900 nm, 800 nm, 700 nm, 600 nm, 500 nm, 400 nm, 300 nm, 200 nm, 100 nm, 75 nm, 50 nm, 40 nm, 30 nm, 20 nm, or 10 nm. For example, a population of multifunctional nanoparticles can desirably have an average diameter of no greater than 100 nm. A population of multifunctional nanoparticles can have a narrow size distribution, for example having diameters with a standard deviation of no greater than 20%, no greater than 15%, no greater than 10%, or no greater than 5%.

In some embodiments, the average diameter of first population 110 can be no greater than 100 nm, no greater than 50 nm, no greater than 40 nm, no greater than 30 nm, no greater than 20 nm, or no greater than 10 nm. Similarly, the average diameter of second population 120 can be no greater than 100 nm, no greater than 50 nm, no greater than 40 nm, no greater than 30 nm, no greater than 20 nm, or no greater than 10 nm. The average diameter of a population of multifunctional nanoparticles can be no greater than 500 nm, no greater than 400 nm, no greater than 300 nm, no greater than 200 nm, or no greater than 100 nm. Thus, in some cases, a population of multifunctional nanoparticles can have an average diameter of no greater than 500 nm and include a first population 110 having an average diameter no greater than 50 nm, and a second population 120 having an average diameter no greater than 50 nm.

The internal structure of multifunctional nanoparticles can be homogenous or heterogeneous. A homogenous internal structure means that two or more populations of nanoparticles in the multifunctional nanoparticle are substantially evenly distributed within the multifunctional nanoparticle, with no organization of one population relative to the other. A heterogeneous internal structure means that nanoparticles of one population can be localized relative to the nanoparticles of another population; for example, the two populations can be segregated within the multifunctional nanoparticle. One form of a heterogeneous internal structure is a "core/shell" configuration, in which nanoparticles of one population cluster together toward the center (or core) of the multifunctional nanoparticle, while nanoparticles of another population are segregated toward the exterior (or shell) of the multifunctional nanoparticle.

Polymeric microbeads in which different-sized quantum dots are embedded with a particle size of 1.2 μm have been described (Han et al., Nature Biotech. 19, 2001, 631-635, which is incorporated by reference in its entirety). U.S. Pat. No. 7,229,690, which is incorporated by reference in its entirety, describes microparticles including a central region and a peripheral region which includes nanoparticles covalently linked to the material of the peripheral region.

A multifunctional nanoparticle can be used to study a living organism, including but not limited to cells and mouse models. Because a multifunctional nanoparticle can be both magnetic and photoluminescent, a cell containing a multifunctional nanoparticle can be manipulated by magnetic force and changes in the cell can be tracked by using fluorescence microscopy. A multifunctional nanoparticle can also be injected into an organ or tissue, such as a brain tumor. The signal of the multifunctional nanoparticle in the organ or tissue can be measured using magnetic resonance images and fluorescence images.

Semiconductor Nanocrystals

Semiconductor nanocrystals demonstrate quantum confinement effects in their luminescence properties. When semiconductor nanocrystals are illuminated with a primary energy source, a secondary emission of energy occurs at a frequency related to the band gap of the semiconductor material used in the nanocrystal. In quantum confined particles, the frequency is also related to the size of the nanocrystal.

The semiconductor forming the nanocrystals can include a Group II-VI compound, a Group II-V compound, a Group III-VI compound, a Group III-V compound, a Group IV-VI compound, a Group I-III-VI compound, a Group II-IV-VI compound, or a Group II-IV-V compound, for example, ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, TlSb, TlSb, PbS, PbSe, PbTe, $Cd_3As_2$, $Cd_3P_2$ or mixtures thereof.

In general, the method of manufacturing a nanocrystal is a colloidal growth process. See, for example, U.S. Pat. Nos. 6,322,901, 6,576,291, and 7,253,452, and U.S. patent application Ser. No. 12/862,195, filed Aug. 24, 2010, each of which is incorporated by reference in its entirety. Colloidal growth can result when an M-containing compound and an X donor are rapidly injected into a hot coordinating solvent. The coordinating solvent can include an amine. The M-containing compound can be a metal, an M-containing salt, or an M-containing organometallic compound. The injection produces a nucleus that can be grown in a controlled manner to form a nanocrystal. The reaction mixture can be gently heated to grow and anneal the nanocrystal. Both the average size and the size distribution of the nanocrystals in a sample are dependent on the growth temperature. In some circumstances, the growth temperature necessary to maintain steady growth increases with increasing average crystal size. The nanocrystal is a member of a population of nanocrystals. As a result of the discrete nucleation and controlled growth, the population of nanocrystals obtained has a narrow, monodisperse distribution of diameters. The monodisperse distribution of diameters can also be referred to as a size. The process of controlled growth and annealing of the nanocrystals in the coordinating solvent that follows nucleation can also result in uniform surface derivatization and regular core structures. As the size distribution sharpens, the temperature can be raised to maintain steady growth. By adding more M-containing compound or X donor, the growth period can be shortened. When adding more M-containing compound or X donor after the initial injection, the addition can be relatively slow, e.g., in several discrete portions added at intervals, or a slow continuous addition. Introducing can include heating a composition including the coordinating solvent and the M-containing compound, rapidly adding a first portion of the X donor to the composition, and slowly adding a second portion of the X donor. Slowly adding the second portion can include a substantially continuous slow addition of the second portion. See, for example, U.S. patent application Ser. No. 13/348,126 which was filed on Jan. 11, 2012, which is incorporated by reference in its entirety. See also U.S. patent application Ser. No. 13/421,527 which was filed on Mar. 15, 2012, which is incorporated by reference in its entirety.

The M-containing salt can be a non-organometallic compound, e.g., a compound free of metal-carbon bonds. M can be cadmium, zinc, magnesium, mercury, aluminum, gallium, indium, thallium, or lead. The M-containing salt can be a metal halide, metal carboxylate, metal carbonate, metal hydroxide, metal oxide, or metal diketonate, such as a metal acetylacetonate. The M-containing salt is less expensive and safer to use than organometallic compounds, such as metal alkyls. For example, the M-containing salts are stable in air, whereas metal alkyls are generally unstable in air. M-containing salts such as 2,4-pentanedionate (i.e., acetylacetonate (acac)), halide, carboxylate, hydroxide, oxide, or carbonate salts are stable in air and allow nanocrystals to be manufactured under less rigorous conditions than corresponding metal alkyls. In some cases, the M-containing salt can be a long-chain carboxylate salt, e.g., a $C_8$ or higher (such as $C_8$ to $C_{20}$, or $C_{12}$ to $C_{18}$), straight chain or branched, saturated or unsaturated carboxylate salt. Such salts include, for example, M-containing salts of lauric acid, myristic acid, palmitic acid, stearic acid, arachidic acid, palmitoleic acid, oleic acid, linoleic acid, linolenic acid, or arachidonic acid.

Suitable M-containing salts include cadmium acetylacetonate, cadmium iodide, cadmium bromide, cadmium chloride, cadmium hydroxide, cadmium carbonate, cadmium acetate, cadmium myristate, cadmium oleate, cadmium oxide, zinc acetylacetonate, zinc iodide, zinc bromide, zinc chloride, zinc hydroxide, zinc carbonate, zinc acetate, zinc myristate, zinc oleate, zinc oxide, magnesium acetylacetonate, magnesium iodide, magnesium bromide, magnesium chloride, magnesium hydroxide, magnesium carbonate, magnesium acetate, magnesium myristate, magnesium oleate, magnesium oxide, mercury acetylacetonate, mercury iodide, mercury bromide, mercury chloride, mercury hydroxide, mercury carbonate, mercury acetate, mercury myristate, mercury oleate, aluminum acetylacetonate, aluminum iodide, aluminum bromide, aluminum chloride, aluminum hydroxide, aluminum carbonate, aluminum acetate, aluminum myristate, aluminum oleate, gallium acetylacetonate, gallium iodide, gallium bromide, gallium chloride, gallium hydroxide, gallium carbonate, gallium acetate, gallium myristate, gallium oleate, indium acetylacetonate, indium iodide, indium bromide, indium chloride, indium hydroxide, indium carbonate, indium acetate, indium myristate, indium oleate, thallium acetylacetonate, thallium iodide, thallium bromide, thallium chloride, thallium hydroxide, thallium carbonate, thallium acetate, thallium myristate, or thallium oleate.

Prior to combining the M-containing salt with the X donor, the M-containing salt can be contacted with a coordinating solvent to form an M-containing precursor. Typical coordinating solvents include alkyl phosphines, alkyl phosphine oxides, alkyl phosphonic acids, or alkyl phosphinic acids; however, other coordinating solvents, such as pyridines, furans, and amines may also be suitable for the nanocrystal production. Examples of suitable coordinating solvents include pyridine, tri-n-octyl phosphine (TOP) and tri-n-octyl phosphine oxide (TOPO). Technical grade TOPO can be used. The coordinating solvent can include a 1,2-diol or an aldehyde. The 1,2-diol or aldehyde can facilitate reaction between the M-containing salt and the X donor and improve the growth process and the quality of the nanocrystal obtained in the process. The 1,2-diol or aldehyde can be a $C_6$-$C_{20}$ 1,2-diol or a $C_6$-$C_{20}$ aldehyde. A suitable 1,2-diol is 1,2-hexadecanediol or myristol and a suitable aldehyde is dodecanal is myristic aldehyde.

The X donor is a compound capable of reacting with the M-containing salt to form a material with the general formula MX. Typically, the X donor is a chalcogenide donor or a pnictide donor, such as a phosphine chalcogenide, a bis(silyl) chalcogenide, dioxygen, an ammonium salt, or a tris(silyl) pnictide. Suitable X donors include dioxygen, elemental sulfur, bis(trimethylsilyl) selenide ((TMS)$_2$Se), trialkyl phosphine selenides such as (tri-n-octylphosphine) selenide (TOPSe) or (tri-n-butylphosphine) selenide (TBPSe), trialkyl phosphine tellurides such as (tri-n-octylphosphine) telluride (TOPTe) or hexapropylphosphorustriamide telluride (HPPTTe), bis(trimethylsilyl)telluride ((TMS)$_2$Te), sulfur, bis(trimethylsilyl)sulfide ((TMS)$_2$S), a trialkyl phosphine sulfide such as (tri-n-octylphosphine) sulfide (TOPS), tris(dimethylamino) arsine, an ammonium salt such as an ammonium halide (e.g., NH$_4$Cl), tris(trimethylsilyl) phosphide ((TMS)$_3$P), tris(trimethylsilyl) arsenide ((TMS)$_3$As), or tris(trimethylsilyl) antimonide ((TMS)$_3$Sb). In certain embodiments, the M donor and the X donor can be moieties within the same molecule.

The X donor can be a compound of formula (I):

X(Y(R)$_3$)$_3$                                                                                        (I)

where X is a group V element, Y is a group IV element, and each R, independently, is alkyl, alkenyl, alkynyl, cycloalkyl, cycloalkenyl, heterocyclyl, aryl, or heteroaryl, where each R, independently, is optionally substituted by 1 to 6 substituents independently selected from hydrogen, halo, hydroxy, nitro, cyano, amino, alkyl, cycloalkyl, cycloalkenyl, alkoxy, acyl, thio, thioalkyl, alkenyl, alkynyl, cycloalkenyl, heterocyclyl, aryl, or heteroaryl. See, e.g., provisional U.S. patent application Ser. No. 61/535,597, filed Sep. 16, 2011, which is incorporated by reference in its entirety.

In some embodiments, X can be N, P, As, or Sb. Y can be C, Si, Ge, Sn, or Pb. Each R, independently, can be alkyl or cycloalkyl. In some cases, each R, independently, can be unsubstituted alkyl or unsubstituted cycloalkyl, for example, a $C_1$ to $C_8$ unsubstituted alkyl or a $C_3$ to $C_8$ unsubstituted cycloalkyl. In some embodiments, X can be P, As, or Sb. In some embodiments, Y can be Ge, Sn, or Pb.

In some embodiments, X can be P, As, or Sb, Y can be Ge, Sn, or Pb, and each R, independently, can be unsubstituted alkyl or unsubstituted cycloalkyl, for example, a $C_1$ to $C_8$ unsubstituted alkyl or a $C_3$ to $C_8$ unsubstituted cycloalkyl. Each R, independently, can be unsubstituted alkyl, for example, a $C_1$ to $C_6$ unsubstituted alkyl.

Alkyl is a branched or unbranched saturated hydrocarbon group of 1 to 30 carbon atoms, such as methyl, ethyl, n-propyl, isopropyl, n-butyl, isobutyl, t-butyl, octyl, decyl, tetradecyl, hexadecyl, eicosyl, tetracosyl and the like. Optionally, an alkyl group can be substituted by 1 to 6 substituents independently selected from hydrogen, halo, hydroxy, nitro, cyano, amino, alkyl, cycloalkyl, cycloalkenyl, alkoxy, acyl, thio, thioalkyl, alkenyl, alkynyl, cycloalkenyl, heterocyclyl, aryl, or heteroaryl. Optionally, an alkyl group can contain 1 to 6 linkages selected from —O—, —S—, —M— and —NR— where R is hydrogen, or $C_1$-$C_8$ alkyl or lower alkenyl. Cycloalkyl is a cyclic saturated hydrocarbon group of 3 to 10 carbon atoms, such as cyclopropyl, cyclobutyl, cyclopentyl, cyclohexyl, cycloheptyl, cyclooctyl, and the like. A cycloalkyl group can be optionally substituted, or contain linkages, as an alkyl group does.

Alkenyl is a branched or unbranched unsaturated hydrocarbon group of 2 to 20 carbon atoms containing at least one double bond, such as vinyl, propenyl, butenyl, and the like. Cycloalkenyl is a cyclic unsaturated hydrocarbon group of 3 to 10 carbon atoms including at least one double bond. An alkenyl or cycloalkenyl group can be optionally substituted, or contain linkages, as an alkyl group does.

Alkynyl is a branched or unbranched unsaturated hydrocarbon group of 2 to 20 carbon atoms containing at least one triple bond, such as ethynyl, propynyl, butynyl, and the like. An alkynyl group can be optionally substituted, or contain linkages, as an alkyl group does.

Heterocyclyl is a 3- to 10-membered saturated or unsaturated cyclic group including at least one ring heteroatom selected from O, N, or S. A heterocylyl group can be optionally substituted, or contain linkages, as an alkyl group does.

Aryl is a 6- to 14-membered carbocyclic aromatic group which may have one or more rings which may be fused or unfused. In some cases, an aryl group can include an aromatic ring fused to a non-aromatic ring. Exemplary aryl groups include phenyl, naphthyl, or anthracenyl. Heteroaryl is a 6- to 14-membered aromatic group which may have one or more rings which may be fused or unfused. In some cases, a heteroaryl group can include an aromatic ring fused to a non-aromatic ring. An aryl or heteroaryl group can be optionally substituted, or contain linkages, as an alkyl group does.

Examples of X donors of formula (I) include: tris(trimethylgermyl)nitride, N(Ge(CH$_3$)$_3$)$_3$; tris(trimethylstannyl) nitride, N(Sn(CH$_3$)$_3$)$_3$; tris(trimethylplumbyl)nitride, N(Pb (CH$_3$)$_3$)$_3$; tris(trimethylgermyl)phosphide, P(Ge(CH$_3$)$_3$)$_3$; tris(trimethylstannyl) phosphide, P(Sn(CH$_3$)$_3$)$_3$; tris(trimethylplumbyl) phosphide, $P(Pb(CH_3)_3)_3$; tris(trimethylgermyl)arsine, $As(Ge(CH_3)_3)_3$; tris(trimethylstannyl)arsine, $As(Sn(CH_3)_3)_3$; tris(trimethylplumbyl)arsine, $As(Pb(CH_3)_3)_3$; tris(trimethylgermyl)stibine, $Sb(Ge(CH_3)_3)_3$; tris(trimethylstannyl)stibine, $Sb(Sn(CH_3)_3)_3$; or tris(trimethylplumbyl)stibine, $Sb(Pb(CH_3)_3)_3$.

For given values of X and R, varying Y can produce X donors having varying reactivity, e.g., different reaction kinetics in the formation of semiconductor nanocrystals. Thus, the reactivity of tris(trimethylsilyl)arsine in the formation of nanocrystals can be different from the reactivity of tris(trimethylstannyl)arsine or tris(trimethylplumbyl)arsine in an otherwise similar reaction. Likewise, for given values of X and Y, variations in R can produce variations in reactivity. In the formation of nanocrystals, reactivity (and particularly reaction kinetics) can affect the size and size distribution of the resulting population of nanocrystals. Thus, selection of precursors having appropriate reactivity can aid in forming a population of nanocrystals having desirable properties, such as a particular desired size and/or a narrow size distribution.

One of the methods for synthesis of semiconductor nanocrystals is injecting a metal and an X donor into a solvent. The X donor can by any listed above such as a chalcogenide donor, a pnictide donor, dioxygen or elemental sulfur. For example, injecting a metal and an S precursor separately into a hot organic solvent in the presence of surfactants. In this method (alkylsilyl) sulfur or elemental sulfur powder dissolved in a carrier solvent have been used as the S precursor. See, for example, Chestnoy, N, et al., 1986, *J. Phys. Chem.*, 90, 3393; Murray, C. B., 1993 J. Am. Chem. Soc., 115, 8706; Yu, W. W. and Peng, X., 2002 *Angew. Chem. Int. Edn.*, 41, 2368; Peng, Z. A. and Peng, X., 2001, *J. Am. Chem. Soc.*, 123, 183; Jang, E., et al. 2004, *J. Phys. Chem. B*, 108, 4597; Joo, J., et al., 2003, *J. Am. Chem. Soc.*, 125, 11100; Cao, Y. C. and Wang, J. 2004, *J. Am. Chem. Soc.*, 126, 14336; and Yu, Z. et al. 2003, *J. Phys. Chem. B.*, 107, 5670, each of which is incorporated by reference in its entirety. The (alkylsilyl) sulfur is a highly reactive precursor because of the easily cleavable S—Si bond. However, the reaction can have certain drawbacks like increased reactivity and sensitivity to air. The sulfur powder dissolved in organic solvents, such as trioctylphosphine (TOP) and oleylamine (OAm), could make a more stable S-P coordinating complex or S-coordinating complex than (alkylsilyl) sulfur. However, TOP and OAm are very sensitive to oxygen so that the synthetic process might not be reliable depending on exposure to air as well as the purity of the compounds. A non-coordinating solvent such as octadecene could be a more stable carrier solvent for sulfur, but sulfur has quite limited solubility. See, for example, Jun, S., et al. 2006, *Nanotechnology*, 17: 4806-4810, which is incorporated by reference in its entirety.

Metal sulfide nanocrystals such as CdS, ZnS and PbS and metal sulfide-coated nanocrystals such as CdSe/CdS and CdTe/CdS can be synthesized by using an alkyl thiol as the sulfur precursor. Alkyl thiols can be desirable for semiconductor nanocrystal synthesis because they are miscible with most organic solvents and stable in air. CdS nanocrystals can be made from CdO and thiols with different alkyl chains such as n-octanethiol and octadecanethiol. The semiconductor nanocrystals can exhibit uniform size, highly crystalline structure and a sharp photoluminescence spectrum. Also, CdSe/CdS core-shell nanocrystals can be prepared by single injection of a mixture consisting of alkyl thiol and Se in trioctylphosphine to a Cd precursor. Alkyl thiols can react with the metal precursor to form stable metal thiolate intermediates during the initial period of reaction, and the thiolate decomposes slowly to form homogeneous nuclei. See, for example, Jun, S., et al. 2006, Nanotechnology, 17, 4806, which has been incorporated by reference in its entirety.

A coordinating solvent can help control the growth of the nanocrystal. The coordinating solvent is a compound having a donor lone pair that, for example, has a lone electron pair available to coordinate to a surface of the growing nanocrystal. Solvent coordination can stabilize the growing nanocrystal. Typical coordinating solvents include alkyl phosphines, alkyl phosphine oxides, alkyl phosphonic acids, or alkyl phosphinic acids, however, other coordinating solvents, such as pyridines, furans, and amines may also be suitable for the nanocrystal production. Examples of suitable coordinating solvents include pyridine, tri-n-octyl phosphine (TOP), tri-n-octyl phosphine oxide (TOPO) or tris-hydroxylpropylphosphine (tHPP). Technical grade TOPO can be used.

The nanocrystal manufactured from an M-containing salt can grow in a controlled manner when the coordinating solvent includes an amine. The amine in the coordinating solvent can contribute to the quality of the nanocrystal obtained from the M-containing salt and X donor. The coordinating solvent can be a mixture of the amine and an alkyl phosphine oxide. The combined solvent can decrease size dispersion and can improve photoluminescence quantum yield of the nanocrystal. The amine can be a primary alkyl amine or a primary alkenyl amine, such as a $C_2$-$C_{20}$ alkyl amine, a $C_2$-$C_{20}$ alkenyl amine, preferably a $C_8$-$C_{18}$ alkyl amine or a $C_8$-$C_{18}$ alkenyl amine. For example, suitable amines for combining with tri-octylphosphine oxide (TOPO) include 1-hexadecylamine, or oleylamine. When the 1,2-diol or aldehyde and the amine are used in combination with the M-containing salt to form a population of nanocrystals, the photoluminescence quantum efficiency and the distribution of nanocrystal sizes are improved in comparison to nanocrystals manufactured without the 1,2-diol or aldehyde or the amine.

The nanocrystal can be a member of a population of nanocrystals having a narrow size distribution. The nanocrystal can be a sphere, rod, disk, or other shape. The nanocrystal can include a core of a semiconductor material. The nanocrystal can include a core having the formula MX (e.g., for a II-VI semiconductor material) or $M_3X_2$ (e.g., for a II-V semiconductor material), where M is cadmium, zinc, magnesium, mercury, aluminum, gallium, indium, thallium, or mixtures thereof, and X is oxygen, sulfur, selenium, tellurium, nitrogen, phosphorus, arsenic, antimony, or mixtures thereof.

The emission from the nanocrystal can be a narrow Gaussian emission band that can be tuned through the complete wavelength range of the ultraviolet, visible, or infrared regions of the spectrum by varying the size of the nanocrystal, the composition of the nanocrystal, or both. For example, both CdSe and CdS can be tuned in the visible region and InAs can be tuned in the infrared region. $Cd_3As_2$ can be tuned from the visible through the infrared.

A population of nanocrystals can have a narrow size distribution. The population can be monodisperse and can exhibit less than a 15% rms deviation in diameter of the nanocrystals, preferably less than 10%, more preferably less than 5%. Spectral emissions in a narrow range of between 10 and 100 nm full width at half max (FWHM) can be observed. Semiconductor nanocrystals can have emission quantum efficiencies (i.e., quantum yields, QY) of greater than 2%, 5%, 10%, 20%, 40%, 60%, 70%, 80%, or 90%. In some cases, semiconductor nanocrystals can have a QY of at least 90%, at least 91%, at least 92%, at least 93%, at least 94%, at least 95%, at least 96%, at least 97%, at least 97%, at least 98%, or at least 99%.

Size distribution during the growth stage of the reaction can be estimated by monitoring the absorption line widths of the particles. Modification of the reaction temperature in response to changes in the absorption spectrum of the particles allows the maintenance of a sharp particle size distribution during growth. Reactants can be added to the nucleation solution during crystal growth to grow larger crystals. By stopping growth at a particular nanocrystal average diameter and choosing the proper composition of the semiconducting material, the emission spectra of the nanocrystals can be tuned continuously over the wavelength range of 300 nm to 5 microns, or from 400 nm to 800 nm for CdSe and CdTe. The nanocrystal has a diameter of less than 150 Å. A population of nanocrystals has average diameters in the range of 15 Å to 125 Å.

The nanocrystal can be a member of a population of nanocrystals having a narrow size distribution. The nanocrystal can be a sphere, rod, disk, or other shape. The nanocrystal can include a core of a semiconductor material. The nanocrystal can include a core having the formula MX, where M is cadmium, zinc, magnesium, mercury, aluminum, gallium, indium, thallium, or mixtures thereof, and X is oxygen, sulfur, selenium, tellurium, nitrogen, phosphorus, arsenic, antimony, or mixtures thereof.

The core can have an overcoating on a surface of the core. The overcoating can be a semiconductor material having a composition different from the composition of the core. The overcoat of a semiconductor material on a surface of the nanocrystal can include a Group II-VI compound, a Group II-V compound, a Group III-VI compound, a Group III-V compound, a Group IV-VI compound, a Group I-III-VI compound, a Group II-IV-VI compound, and a Group II-IV-V compound, for example, ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, TlSb, TlSb, PbS, PbSe, PbTe, $Cd_3As_2$, $Cd_3P_2$ or mixtures thereof. For example, ZnS, ZnSe or CdS overcoatings can be grown on CdSe or CdTe nanocrystals. An overcoating process is described, for example, in U.S. Pat. No. 6,322,901. By adjusting the temperature of the reaction mixture during overcoating and monitoring the absorption spectrum of the core, over coated materials having high emission quantum efficiencies and narrow size distributions can be obtained. The overcoating can be between 1 and 10 monolayers thick.

Shells are formed on nanocrystals by introducing shell precursors at a temperature where material adds to the surface of existing nanocrystals but at which nucleation of new particles is rejected. In order to help suppress nucleation and anisotropic elaboration of the nanocrystals, selective ionic layer adhesion and reaction (SILAR) growth techniques can be applied. See, e.g., U.S. Pat. No. 7,767,260, which is incorporated by reference in its entirety. In the SILAR approach, metal and chalcogenide precursors are added separately, in an alternating fashion, in doses calculated to saturate the available binding sites on the nanocrystal surfaces, thus adding one-half monolayer with each dose. The goals of such an approach are to: (1) saturate available surface binding sites in each half-cycle in order to enforce isotropic shell growth; and (2) avoid the simultaneous presence of both precursors in solution so as to minimize the rate of homogenous nucleation of new nanoparticles of the shell material.

In the SILAR approach, it can be beneficial to select reagents that react cleanly and to completion at each step. In other words, the reagents selected should produce few or no reaction by-products, and substantially all of the reagent added should react to add shell material to the nanocrystals. Completion of the reaction can be favored by adding sub-stoichiometric amounts of the reagent. In other words, when less than one equivalent of the reagent is added, the likelihood of any unreacted starting material remaining is decreased.

The quality of core-shell nanocrystals produced (e.g., in terms of size monodispersity and QY) can be enhanced by using a constant and lower shell growth temperature. Alternatively, high temperatures may also be used. In addition, a low-temperature or room temperature "hold" step can be used during the synthesis or purification of core materials prior to shell growth.

Another approach to forming a shell on a nanocrystal core includes dissolving the cores in a coordinating solvent and then heating the mixture to between 200° C. and 350° C. At that point, a calculated amount of an M-containing compound and X donor can be slowly infused into the growth solution containing the dissolved nanocrystal cores. The slow infusion process includes adding the M-containing compound and the X donor at a rate of between 0.03 mL/min and 0.07 mL/min by using a syringe pump or any method that would allow for controlled, slow and steady addition. The final core-shell nanocrystals can be subjected to higher temperatures for further annealing, if desired. After the slow infusion, additional ligands may be added to the mixture. The shell overcoating via slow infusion can result in high quality core-shell nanocrystals with a narrow size distribution, narrow photoluminescence peak width, high photoluminescence quantum yield, and reduced single dot blinking as compared to semiconductor nanocrystals prepared by other methods.

The outer surface of the nanocrystal can include a layer of compounds derived from the coordinating agent used during the growth process. The surface can be modified by repeated exposure to an excess of a competing coordinating group to form an overlayer. For example, a dispersion of the capped nanocrystal can be treated with a coordinating organic compound, such as pyridine, to produce crystals which disperse readily in pyridine, methanol, and aromatics but no longer disperse in aliphatic solvents. Such a surface exchange process can be carried out with any compound capable of coordinating to or bonding with the outer surface of the nanocrystal, including, for example, phosphines, thiols, amines and phosphates. The nanocrystal can be exposed to short chain polymers which exhibit an affinity for the surface and which terminate in a moiety having an affinity for a suspension or dispersion medium. Such affinity improves the stability of the suspension and discourages flocculation of the nanocrystal. Nanocrystal coordinating compounds are described, for example, in U.S. Pat. No. 6,251,303, which is incorporated by reference in its entirety.

Monodentate alkyl phosphines (and phosphine oxides; the term phosphine below will refer to both) can passivate nanocrystals efficiently. When nanocrystals with conventional monodentate ligands are diluted or embedded in a non-passivating environment (i.e., one where no excess ligands are present), they tend to lose their high luminescence. Typical are an abrupt decay of luminescence, aggregation, and/or phase separation. In order to overcome these limitations, polydentate ligands can be used, such as a family of polydentate oligomerized phosphine ligands. The polydentate ligands show a high affinity between ligand and nanocrystal surface. In other words, they are stronger ligands, as is expected from the chelate effect of their polydentate characteristics.

In general, a ligand for a nanocrystal can include a first monomer unit including a first moiety having affinity for a surface of the nanocrystal, a second monomer unit including a second moiety having a high water solubility, and a third monomer unit including a third moiety having a selectively reactive functional group or a selectively binding functional group. In this context, a "monomer unit" is a portion of a polymer derived from a single molecule of a monomer. For example, a monomer unit of poly(ethylene) is —$CH_2CH_2$—, and a monomer unit of poly(propylene) is —$CH_2CH(CH_3)$—. A "monomer" refers to the compound itself, prior to polymerization, e.g., ethylene is a monomer of poly(ethylene) and propylene of poly(propylene).

A moiety having high water solubility typically includes one or more ionized, ionizable, or hydrogen bonding groups, such as, for example, an amine, an alcohol, a carboxylic acid, an amide, an alkyl ether, a thiol, or other groups known in the art. Moieties that do not have high water solubility include, for example, hydrocarbyl groups such as alkyl groups or aryl groups, haloalkyl groups, and the like. High water solubility can be achieved by using multiple instances of a slightly soluble group: for example, diethyl ether is not highly water soluble, but a poly(ethylene glycol) having multiple instances of a —$CH_2$—O—$CH_2$— alkyl ether group can be highly water soluble.

For example, the ligand can include a polymer including a random copolymer. The random copolymer can be made using any method of polymerization, including cationic, anion, radical, metathesis or condensation polymerization, for example, living cationic polymerization, living anionic polymerization, ring opening metathesis polymerization, group transfer polymerization, free radical living polymerization, living Ziegler-Natta polymerization, or reversible addition fragmentation chain transfer (RAFT) polymerization. See, for example, U.S. patent application Ser. No. 12/857,430, filed on Aug. 16, 2010 and U.S. patent application Ser. No. 13/069,458, filed on Mar. 23, 2011, each of which is incorporated by reference in its entirety.

In some cases, M belongs to group II and X belongs to group VI, such that the resulting semiconductor nanocrystal includes a II-VI semiconductor material. For example, the M-containing compound can be a cadmium-containing compound and the X donor can be a selenium donor or an sulfur donor, such that the resulting semiconductor nanocrystal includes a cadmium selenide semiconductor material or a cadmium sulfide semiconductor material, respectively.

The particle size distribution can be further refined by size selective precipitation with a poor solvent for the nanocrystals, such as methanol/butanol as described in U.S. Pat. No. 6,322,901. For example, nanocrystals can be dispersed in a solution of 10% butanol in hexane. Methanol can be added dropwise to this stirring solution until opalescence persists. Separation of supernatant and flocculate by centrifugation produces a precipitate enriched with the largest crystallites in the sample. This procedure can be repeated until no further sharpening of the optical absorption spectrum is noted. Size-selective precipitation can be carried out in a variety of solvent/nonsolvent pairs, including pyridine/hexane and chloroform/methanol. The size-selected nanocrystal population can have no more than a 15% rms deviation from mean diameter, preferably 10% rms deviation or less, and more preferably 5% rms deviation or less.

More specifically, the coordinating ligand can have the formula:

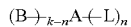

wherein k is 2, 3 or 5, and n is 1, 2, 3, 4 or 5 such that k–n is not less than zero; A is O, S, S=O, $SO_2$, Se, Se=O, N, N=O, P, P=O, As, or As=O; each of B and L, independently, is aryl, heteroaryl, or a straight or branched $C_{2-12}$ hydrocarbon chain optionally containing at least one double bond, at least one triple bond, or at least one double bond and one triple bond. The hydrocarbon chain can be optionally substituted with one or more $C_{1-4}$ alkyl, $C_{2-4}$ alkenyl, $C_{2-4}$ alkynyl, $C_{1-4}$ alkoxy, hydroxyl, halo, amino, nitro, cyano, $C_{3-5}$ cycloalkyl, 3-5 membered heterocycloalkyl, aryl, heteroaryl, $C_{1-4}$ alkylcarbonyloxy, $C_{1-4}$ alkyloxycarbonyl, $C_{1-4}$ alkylcarbonyl, or formyl. The hydrocarbon chain can also be optionally interrupted by —O—, —S—, —N($R^a$)—, —N($R^a$)—C(O)—O—, —O—C(O)—N($R^a$)—, —N($R^a$)—C(O)—N($R^b$)—, —O—C(O)—O—, —P($R^a$)—, or —P(O)($R^a$)—. Each of $R^a$ and $R^b$, independently, is hydrogen, alkyl, alkenyl, alkynyl, alkoxy, hydroxylalkyl, hydroxyl, or haloalkyl.

A suitable coordinating ligand can be purchased commercially or prepared by ordinary synthetic organic techniques, for example, as described in J. March, *Advanced Organic Chemistry*, which is incorporated by reference in its entirety.

Transmission electron microscopy (TEM) can provide information about the size, shape, and distribution of the nanocrystal population. Powder X-ray diffraction (XRD) patterns can provide the most complete information regarding the type and quality of the crystal structure of the nanocrystals. Estimates of size are also possible since particle diameter is inversely related, via the X-ray coherence length, to the peak width. For example, the diameter of the nanocrystal can be measured directly by transmission electron microscopy or estimated from X-ray diffraction data using, for example, the Scherrer equation. It also can be estimated from the UV/Vis absorption spectrum.

Magnetic Nanoparticles

A nanoparticle comprising a magnetic material (e.g., a paramagnetic or superparamagnetic material) may include elemental iron, a spinel ferrite ($Fe_3O_4$), or at least one mixed spinel ferrite having the general formula $MFe_2O_4$, where M is a metal having an oxidation state other than exhibited by the predominant form of iron, which is 3+. Non-limiting examples of M include iron (where a portion of the iron present iron is $Fe^{2+}$; i.e., iron having a 2+ oxidation state), copper, titanium, manganese, cobalt, nickel, chromium, gadolinium, zinc, yttrium, molybdenum, and vanadium.

The nanoparticle may be formed by a non-aqueous synthetic route for the formation of monodisperse crystalline nanoparticles, which is described in U.S. Patent Application Publication No. 2004/00229737 and in U.S. Pat. No. 6,797,380, each of which is incorporated by reference in its entirety. Organometallic precursor materials, such as, but not limited to, transition metal carbonyl compounds, are thermally decomposed in a solvent and in the presence of a surfactant and an oxidant. The organometallic precursors are provided in an appropriate stoichiometric ratio to a nonpolar aprotic solvent containing the surfactant and the oxidant.

A nonpolar aprotic organic solvent is combined with an oxidant and a first surfactant. The nonpolar aprotic solvent is thermally stable at the temperatures at which the plurality of nanoparticles are formed. In one embodiment, the nonpolar aprotic solvent has a boiling point in the range from about 275° C. to about 340° C. Suitable nonpolar aprotic solvents include, but are not limited to, dioctyl ether, hexadecane, trioctylamine, tetraethylene glycol dimethyl ether (also known as "tetraglyme"), and combinations thereof. The oxidant comprises at least one of an organo-tertiary amine oxide, a peroxide, an alkylhydroperoxide, a peroxyacid, molecular oxygen, nitrous oxide, and combinations thereof. In one embodiment, the oxidant comprises an organo-tertiary amine oxide having at least one methyl group. One non-limiting example of such an oxidant is trimethyl amine oxide.

The first surfactant optionally can include at least one of a polymerizable functionalized group, an initiating functionalized group, and a cross-linking functionalized group. An amount of the first surfactant is provided to the nonpolar aprotic organic solvent to produce a first concentration of the first surfactant in the nonpolar aprotic solvent. The polymerizable functionalized group may comprise at least one of an alkene, an alkyne, a vinyl (including acrylics and styrenics), an epoxide, an azeridine, a cyclic ether, a cyclic ester, and a cyclic amide. The initiating functionalized group may comprise at least one of a thermal or photoinitiator, such as, but not limited to, an azo compound, a hydroxide, a peroxide, an alkyl halide, an aryl halide, a halo ketone, a halo ester, a halo amide, a nitroxide, a thiocarbonyl, a thiol, an organo-cobalt compound, a ketone, and an amine. The cross-linking functionalized group may be one of a thiol, an aldehyde, a ketone, a hydroxide, an isocyanide, an alkyl halide, a carboxylate, a carboxylic acid, a phenol, an amine, and combinations thereof.

At least one organometallic compound is provided to the combined nonpolar aprotic organic solvent, oxidant, and first surfactant. The at least one organometallic compound comprises at least one metal and at least one ligand. The metal may comprise a transition metal, such as, but not limited to, iron, nickel, copper, titanium, cadmium, cobalt, chromium, manganese, vanadium, yttrium, zinc, and molybdenum, or other metals, such as gadolinium. The at least one ligand may comprise at least one of carbonyl group, a cyclo octadienyl group, an organophosphine group, a nitrosyl group, a cyclo pentadienyl group, a pentamethyl cyclo pentadienyl group, a π-acid ligand, a nitroxy group, and combinations thereof. Non-limiting examples of the at least one organometallic compound include iron carbonyl (Fe$(CO)_5$), cobalt carbonyl (Co$(CO)_8$), and manganese carbonyl (Mn$_2$(CO)$_{10}$). In one embodiment, an amount of the at least one organometallic compound is provided to the aprotic solvent such that a ratio of the concentration of the at least one organometallic compound to the concentration of the oxidant has a value in a range from about 1 to about 10.

In one embodiment, a first organometallic compound is provided to the combined nonpolar aprotic organic solvent, oxidant, and first surfactant. The combined first organometallic compound, nonpolar aprotic organic solvent, oxidant, and first surfactant are then preheated under an inert gas atmosphere to a temperature for a time interval. The preheating serves to remove the ligands from the metal cation in the first organometallic compound. In one embodiment, the combined first organometallic compound, nonpolar aprotic organic solvent, oxidant, and first surfactant are preheated to a temperature in a range from about 90° C. to about 140° C. for a time interval ranging from about 15 minutes to about 90 minutes.

In another embodiment, the combined nonpolar aprotic solvent, oxidant, first surfactant, and the at least one organometallic compound are heated to under an inert gas atmosphere to a first temperature and maintained at the first temperature for a first time interval. At this point, the at least one organometallic compound reacts with the oxidant in the presence of the first surfactant and the nonpolar aprotic solvent to form a plurality of nanoparticles, wherein each nanoparticle comprises a crystalline inorganic nanoparticle and at least one outer coating comprising the first surfactant, which is disposed on an outer surface of the inorganic nanoparticle and substantially covers and encloses the substantially crystalline inorganic nanoparticle.

The first temperature to which the combined nonpolar aprotic solvent, oxidant, first surfactant, and the at least one organometallic compound are heated is dependent upon the relative thermal stability of the at least one organometallic compound that is provided to the aprotic solvent. The first temperature is in a range from about 30° C. to about 400° C. In one embodiment, the first temperature is in a range from about 275° C. to about 400° C. and, preferably, in a range from about 275° C. to about 310° C. The length of the first time interval may be from about 30 minutes to about 2 hours, depending on the particular organometallic compounds and oxidants that are provided to the aprotic solvent.

In one embodiment, the method may further comprise the step of precipitating the plurality of nanoparticles from the nonpolar aprotic solvent. Precipitation of the plurality of nanoparticles may be accomplished by adding at least one of an alcohol or a ketone to the nonpolar aprotic solvent. Alcohols such as, but not limited to, methanol and ethanol may be used. Alcohols having at least three carbon atoms, such as isopropanol, are preferred, as their use tends to produce the smallest degree of agglomeration of the plurality of nanoparticles. Ketones such as, but not limited to, acetone may be used in conjunction with—or separate from—an alcohol in the precipitation step.

In another embodiment, the method may also further include a step in which a ligand either partially of completely replaces—or is exchanged for—the first surfactant in the outer coating. Following the formation of the plurality of nanoparticles, the nanoparticles are precipitated and resuspended in a liquid including a desired ligand (e.g., the neat ligand, or a solution of ligand in a solvent compatible with the existing outer coating). This procedure may be repeated as necessary. Alternatively, the ligand is added to the nonpolar aprotic solvent such that the ligand is present in a second concentration, the second concentration being greater than a first concentration of the first surfactant in the nonpolar aprotic solvent. The nanoparticles may be subjected to additional rounds of ligand exchange. For example, it may be desirable to exchange the surfactant for an intermediate ligand which is subsequently exchanged for the desired ligand. The desired ligand can include a ligand of any of formulas (I)-(IV), or a mixture thereof.

In one particular embodiment, a method of forming a plurality of monodisperse crystalline nanoparticles, wherein each of the plurality of monodisperse nanoparticles comprises a crystalline mixed spinel ferrite core and an outer coating disposed on an outer surface of the crystalline mixed spinel ferrite core. The crystalline mixed spinel ferrite core comprises iron in a first oxidation state and a transition metal in a second oxidation state, wherein the second oxidation state is different from the first oxidation state.

In this method, an oxidant and a first surfactant are combined a nonpolar aprotic organic solvent. In one embodiment, the nonpolar aprotic organic solvent has a boiling point in a range from about 275° C. to about 340° C. Suitable nonpolar aprotic solvents include, but are not limited to, dioctyl ether, hexadecane, trioctylamine, trioctylamine, tetraethylene glycol dimethyl ether (also known as "tetraglyme"), and combinations thereof. The oxidant comprises at least one of an organo-tertiary amine oxide, a peroxide, an alkylhydroperoxide, a peroxyacid, molecular oxygen, nitrous oxide, and combinations thereof. In one embodiment, the oxidant comprises an organo-tertiary amine oxide having at least one methyl group. One non-limiting example of such an oxidant is trimethyl amine oxide. The first surfactant optionally can include at least one of a polymerizable functionalized group, an initiating functionalized group, and a cross-linking functionalized group. An amount of the first surfactant is provided to the nonpolar aprotic organic solvent to produce a first concentration of the first surfactant in the nonpolar aprotic solvent. Suitable polymerizable functionalized groups, initiating functionalized groups, and cross-linking functionalized groups for the first surfactant are the same as those that have been previously described herein.

The combined nonpolar aprotic solvent, oxidant, and first surfactant can be heated under an inert gas atmosphere to a first temperature. In one embodiment, the first temperature is in a range from about 90° C. to about 140° C. An organo-iron compound is then provided to the combined nonpolar aprotic solvent, oxidant, and first surfactant at the first temperature. The organo-iron compound, together with the combined nonpolar aprotic solvent, oxidant, and first surfactant, is maintained at the first temperature for a first time interval under an inert gas atmosphere. The ligands are removed from the organo-iron compound in the presence of the oxidant; the first time interval must therefore be of sufficient duration to accomplish the removal. In one embodiment, the first time interval may be from about 15 minutes to about 90 minutes.

The organo-iron compound comprises iron and at least one ligand. In one embodiment, the at least one ligand comprises at least one of a carbonyl group, a cyclo octadienyl group, an organophosphine group, a nitrosyl group, a cyclo pentadienyl group, a pentamethyl cyclo pentadienyl group, a π-acid ligand, a nitroxy group, and combinations thereof. One non-limiting example of the organo-iron compound is iron carbonyl ($Fe(CO)_5$).

Following the expiration of the first time interval, at least one organo-transition metal compound is added to and combined with the organo-iron compound and the combined nonpolar aprotic solvent, oxidant, and first surfactant together at the first temperature. The at least one organo-transition metal compound comprises a transition metal and at least one ligand. In one embodiment, the transition metal is one of iron, nickel, copper, titanium, cobalt, chromium, manganese, vanadium, yttrium, zinc, and molybdenum, and the at least one ligand comprises at least one of a carbonyl group, a cyclo octadienyl group, an organophosphine group, a nitrosyl group, a cyclo pentadienyl group, a pentamethyl cyclo pentadienyl group, a π-acid ligand, a nitroxy group, and combinations thereof. Analogous organo-metallic compounds of selected metals, such as gadolinium, maybe substituted for organo-transition metal compounds. Non-limiting examples of the at least one organo-transition metal compound include cobalt carbonyl ($Co(CO)_8$) and manganese carbonyl ($Mn_2(CO)_{10}$).

The at least one organo-transition metal compound, organo-iron compound, nonpolar aprotic solvent, oxidant, and first surfactant, combined together, are heated to a second temperature and maintained at the second temperature for a second time interval. The organo-iron compound reacts with the at least one organo-transition metal compound at the second temperature to form a plurality of monodisperse nanoparticles, wherein each of the plurality of monodisperse nanoparticles comprises a crystalline mixed spinel ferrite core and an outer coating comprising the first surfactant, disposed on an outer surface of the crystalline mixed spinel ferrite core. Iron carbonyl ($Fe(CO)_5$), for example, may react with cobalt carbonyl ($Co(CO)_8$) to form nanoparticles comprising the crystalline cobalt iron spinel ferrite $CoFe_2O_4$. Alternatively, iron carbonyl may react with manganese carbonyl ($Mn_2(CO)_{10}$) to form nanoparticles comprising the crystalline manganese iron spinel ferrite $MnFe_2O_4$. Where the at least one organo-transition metal compound comprises iron carbonyl, nanoparticles comprising the crystalline mixed γ-iron oxide/ferrite $(\gamma\text{-}Fe_2O_3)_{1-y}(Fe_3O_4)_y$ are formed.

In one embodiment, the second temperature is in a range from about 285° C. to about 400° C. In another embodiment, the second temperature is in a range from about 275° C. to about 310° C. In one embodiment, the second time interval may range from about 30 minutes to about two hours.

The plurality of nanoparticles can be precipitated from the nonpolar aprotic solvent by adding at least one of an alcohol or a ketone to the nonpolar aprotic solvent. Alcohols such as, but not limited to, methanol and ethanol may be used. Alcohols having at least three carbon atoms, such as isopropanol, are preferred, as their use tends to produce the smallest degree of agglomeration. Ketones such as, but not limited to, acetone may be used in conjunction with—or separate from—an alcohol in the precipitation step.

The plurality of nanoparticles produced by the methods described are monodisperse; i.e., the nanoparticles are substantially identical in size and shape.

Other methods are described in U.S. Pat. Nos. 6,962,685 and 7,128,891, each of which is incorporated by reference in its entirety, in which nanoparticles are made by treating a mixture of metal salt, alcohol, an acid and amine with ethanol to precipitate magnetic materials.

Carbon Nanoparticles

Carbon nanoparticles can include for example, carbon nanotubes (e.g., a single-walled or multi-walled carbon nanotube), carbon nanowires, diamonds, graphite, graphene, fullerenes, carbon blacks, carbon nanofibers, or other carbon-based nanostructure.

Carbon nanotubes ("CNT") are macromolecules in the shape of a long, thin cylinder, often with a diameter of a few nanometers. The basic structural element in a carbon nanotube is a hexagon, which is the same as that found in graphite. Based on the orientation of the tube axis with respect to the hexagonal lattice, a carbon nanotube potentially has three different configurations: armchair, zigzag, and chiral (also known as spiral). In armchair configuration, the tube axis is perpendicular to two of six carbon-carbon bonds of the hexagonal lattice. In zigzag configuration, the tube axis is parallel to two of six carbon-carbon bonds of the hexagonal lattice. Both these two configurations are achiral. In chiral configuration, the tube axis forms an angle other than 90 or 180 degrees with any of six carbon-carbon bonds of the hexagonal lattice. Nanotubes with these three configurations often exhibit different physical and chemical properties. For example, an armchair nanotube is always metallic, whereas a zigzag nanotube may be metallic or semiconductive, depending on the diameter of the nanotube. All three types of different configurations of nanotubes are expected to be very good thermal conductors along the tube axis, exhibiting a property known as "ballistic conduction," but are also good insulators laterally to the tube axis.

In addition to the common hexagonal structure, the cylinder of a carbon nanotube may also contain other sized rings, such as pentagons and heptagons. Replacement of some regular hexagons with pentagons and/or heptagons may cause cylinders to bend, twist, or change diameter, and thus lead to some interesting structures such as "Y-," "T-," and "X-junctions," and different physical and chemical properties. These structural variations and configurations can be found in both SWNT and MWNT. The present invention is not limited to any particular configuration and structural variation. The carbon nanotubes used in the present invention may be in the configuration of armchair, zigzag, chiral, or combinations thereof. The carbon nanotubes may also contain structural elements other than hexagon, such as pentagon, heptagon, octagon, or combinations thereof.

Another structural variation, which is specific for MWNT molecules, is the arrangement of multiple tubes in a MWNT molecule. A perfect MWNT is like a stack of graphene sheets rolled up into concentric cylinders, with each wall parallel to the central axis. However, the tubes may also be arranged so that an angle between the graphite basal planes and the tube axis is formed. Such MWNTs are known as a "stacked cone", "Chevron," "bamboo," "ice cream cone," or "piled cone structure." A stacked cone MWNT may reach a diameter of about 100 nm. In spite of these structural variations, all MWNTs are suitable for the present invention, as long as they have excellent thermal conductive properties.

Carbon nanotubes may also encapsulate other elements and/or molecules within their enclosed tubular structures. Such elements include Si, Ti, V, Cr, Mn, Fe, Co, Ni, Cu, Y, Zr, Mo, Ta, Au, Th, La, Ce, Pr, Nb, Gd, Th, Dy, Ho, Er, Tm, Yb, Lu, Mo, Pd, Sn, and W. Such molecules include alloys of these elements such as alloys of cobalt with S, Br, Pb, Pt, Y, Cu, B, and Mg, and compounds such as the carbides (i.e. TiC, MoC, etc.)

Carbon nanoparticles may also be chemically modified or functionalized. Covalent functionalization of carbon nanoparticles, especially carbon nanotubes and fullerenes, has commonly been accomplished by three different approaches, namely, thermally activated chemistry, electrochemical modification, and photochemical functionalization. The most common method of thermally activated chemical functionalization is an addition reaction on the sidewalls. For example, the extensive treatment of a nanotube with concentrated nitric and sulfuric acids leads to the oxidative opening of the tube caps as well as the formation of holes in the sidewalls. This produces a nanotube decorated with carboxyl groups, which can be further modified through the creation of amide and ester bonds to generate a vast variety of functional groups. The nanotube molecule may also be modified through addition reactions with various chemical reagents, such halogens and ozone. Unlike thermally controlled modification, electrochemical modification of nanotubes may be carried out in a more selective and controlled manner. Interestingly, a SWNT can be selectively modified or functionalized either on the cylinder sidewall or the optional end caps. These two structurally distinct moieties often display different chemical and physical characteristics. The functional groups on functionalized carbon nanoparticles may be attached directly to the carbon atoms of a carbon nanoparticle or via chemical linkers, such as alkylene or arylene groups. To increase hydrophilicity, carbon nanoparticles may be functionalized with one or more hydrophilic functional groups, such as sulfonate, carboxyl, hydroxyl, amino, amide, urea, carbamate, urethane, phosphate, and/or functionalized alkyl and aryl groups (e.g., sulfonated p-aminophenyl group). To increase hydrophobicity, carbon nanoparticles may be functionalized with one or more hydrophobic alkyl or aryl groups. The functionalized carbon particle may have no less than about 2, no less than about 5, no less than about 10, no less than about 20, or no less than about 50 functional groups on average.

Metal Nanoparticles and Metal Oxide Nanoparticles

A metal nanoparticle or metal oxide nanoparticle can have a dimension of less than 100 nanometers. The metal of the metal nanoparticle or the metal oxide nanoparticle can include titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, scandium, yttrium, lanthanum, a lanthanide series or actinide series element (e.g., cerium, praseodymium, neodymium, promethium, samarium, europium, gadolinium, terbium, dysprosium, holmium, erbium, thulium, ytterbium, lutetium, thorium, protactinium, or uranium), boron, aluminum, gallium, indium, thallium, silicon, germanium, tin, lead, antimony, bismuth, polonium, magnesium, calcium, strontium, and barium. In certain embodiments, the metal can be iron, ruthenium, cobalt, rhodium, nickel, palladium, platinum, silver, gold, cerium or samarium.

The metal oxide can be an oxide of any of these materials or combination of materials. For example, the metal can be gold, or the metal oxide can be an iron oxide (e.g., $Fe_2O_3$, $Fe_3O_4$), a cobalt oxide (e.g., CoO), a zinc oxide (e.g., ZnO), a cerium oxide (e.g., $CeO_2$), or a titanium oxide (e.g., $TiO_2$). Preparation of metal and metal oxide nanoparticles is described, for example, in U.S. Pat. Nos. 5,897,945 and 6,759,199, each of which is incorporated by reference in its entirety. Suitable metal oxides include but are not limited to $Al_2O_3$ CuO, MgO, $SiO_2$, $GeO_2$, $B_2O_3$, $TeO_2$, $V_2O_5$, $BiO_2$, $Sb_2O_5$, $TiO_2$, ZnO, FeO, $Fe_2O_3$, $Fe_3O_4$, or $CrO_3$.

EXAMPLES

In a typical synthesis, 0.5 mL of a chloroform solution of CdSe/CdS core/shell semiconductor nanocrystals (10 mg/mL) was mixed with 0.5 mL of a chloroform solution of $Fe_3O_4$ magnetic nanoparticles (MPs) (10 mg/mL). Then, the mixture solution was mixed with 1 mL dodecyltrimethylammonium bromide (DTAB) solution (20 mg DTAB in 1 mL Nanopure water). After removing the chloroform by blowing Ar to the solution, a clear water solution contains both semiconductor nanocrystals and MPs was obtained. Afterwards, this water solution was injected into 5 mL an ethyl glycol (EG) solution of poly(vinyl pyrrolidone) (PVP) (MW 5,500) at a concentration of 110 mg/mL under vigorous stirring and kept at room temperature (RT) for 15 min. The final assembled multifunctional nanoparticles can be separated from the reaction solution by centrifugation at 8000 g for 30 min and further dispersed in ethanol.

FIG. 3a shows the typical TEM images of resulting multifunctional assembled nanoparticles with an average size of 63 nm with a relative standard distribution of 11%. HR-TEM image (FIG. 3b) showed that these assembled nanoparticles indeed contained both semiconductor nanocrystals and MPs inside each single particle. This result was consistent with elemental analysis results showed in FIG. 4. Both elemental mapping and line scanning results show that each assembled nanoparticle contains cadmium, sulfur and iron atoms which cadmium and sulfur signals are generated from CdSe/CdS QDs, iron signal is generated from $Fe_3O_4$ magnetic particles (FIG. 4).

Figure 5:
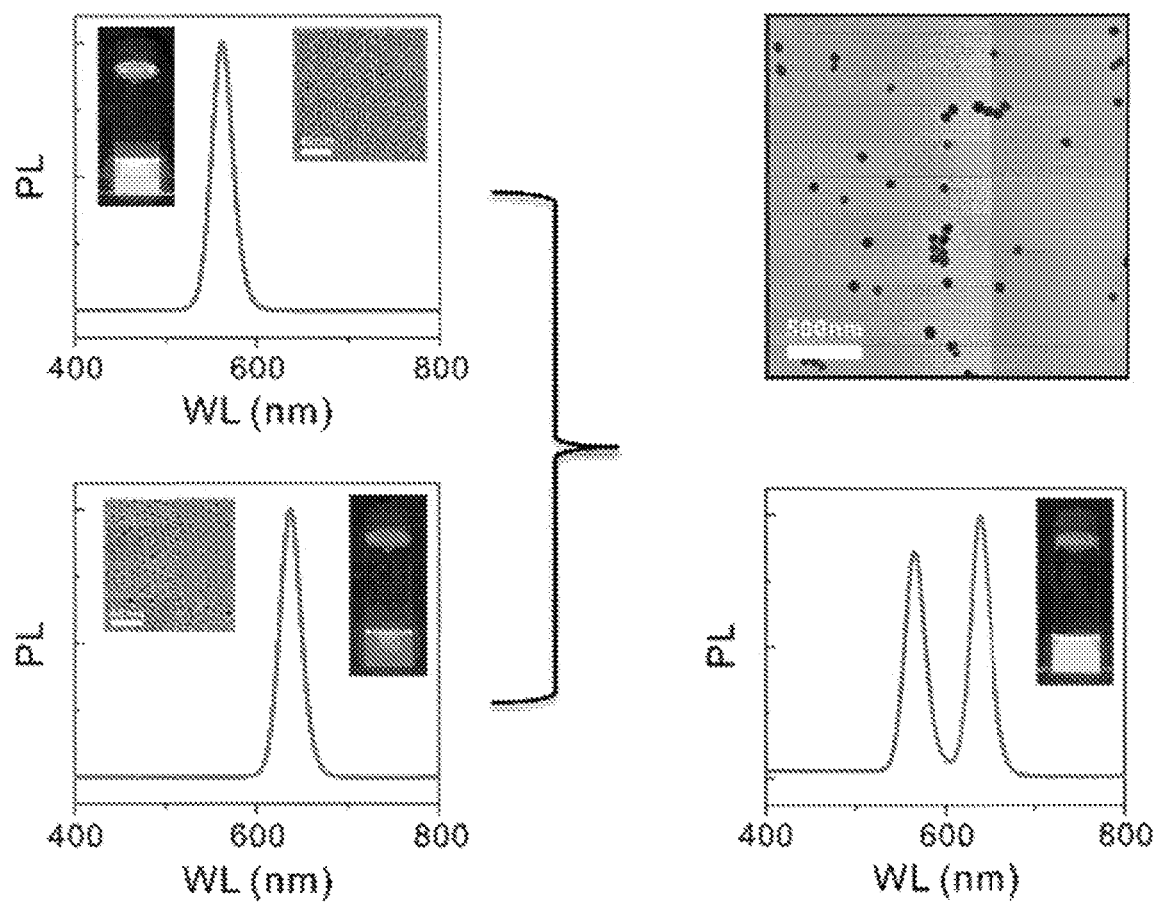
FIG. 5 shows TEM images, fluorescence spectra and photographs (under UV illumination) of green color CdSe/CdS core/shell nanocrystals (up-left), red color CdSe/CdS core/shell nanocrystals (bottom-left) and dual-color assembled multifunctional nanoparticles (right).

FIG. 5 shows that this synthesis method was generalized to synthesize dual-color particles by assembly of green color (PL peak position at 565 nm) nanocrystals (FIG. 5 up-left) and red color (PL peak position at 637 nm) nanocrystals (FIG. 5 bottom-left) to form the final dual-color assembled multifunctional nanoparticles (FIG. 5 right, showing two peaks in the PL spectrum).

Figure 6:
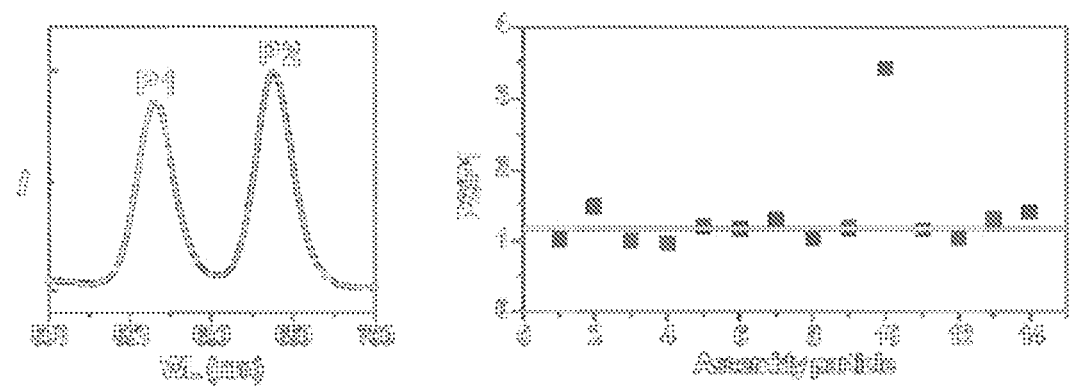
FIG. 6 shows a fluorescence spectrum of dual color multifunctional nanoparticles (left) and the relative fluorescence of a number of dual color multifunctional nanoparticles (right).

FIG. 6 shows that dual color multifunctional nanoparticles were consistent in their relative amounts of each color of nanocrystal present in the multifunctional nanoparticles. The fluorescence spectra of several individual multifunctional nanoparticles were recorded. A representative spectrum in shown on the left in FIG. 6, showing to fluorescence peaks labeled P1 and P2. The relative intensities of P1 and P2 were measured for each of the several individual multifunctional nanoparticles, plotted on the right in FIG. 6. The relative intensity was consistent across the several nanoparticles measured (excluding one outlier shown in FIG. 6).

Figure 7:
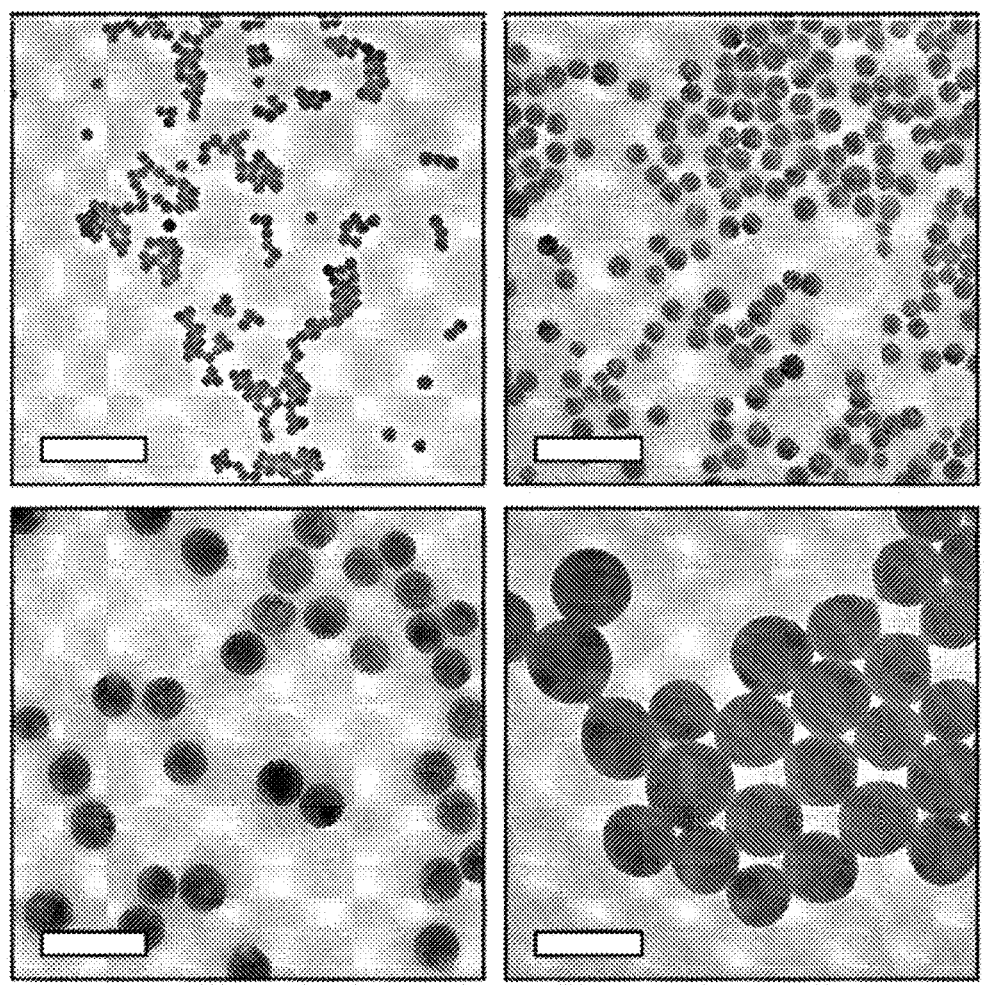
FIG. 7 shows TEM images of multifunctional nanoparticles of controlled sizes with diameters ranging from 50 nm to 350 nm. Scale bars are 500 nm.

FIG. 7 illustrates the size control that was achieved. Multifunctional nanoparticles were prepared in the presence of amphiphilic compounds such as oleic acid and/or oleyl amine, and diameters of the multifunctional nanoparticles in a given preparation were monodisperse; the average diameters could be controlled. Average diameters were in the range of 50 nm to 350 nm (scale bars in FIG. 7 are 500 nm).

To modify these assembled multifunctional nanoparticles with a silica shell, 5 mg of assembled magneto-fluorescent multifunctional nanoparticles were dispersed in 10 ml ethanol. Next, 100 µl of tetraethoxysilane (TEOS), 100 µl NH$_4$OH (28 wt % in water) and 300 µl of deionized water were added to the ethanol solution sequentially under vigorous stirring. The solution was kept at RT with stirring for 12 hrs. The final silica coated assembled multifunctional nanoparticles were collected by centrifugation at 8000 g for 15 min and purified with three cycles of dispersion/centrifugation. The final particles were dissolved in DI water and stored at 4° C.

Figure 8:
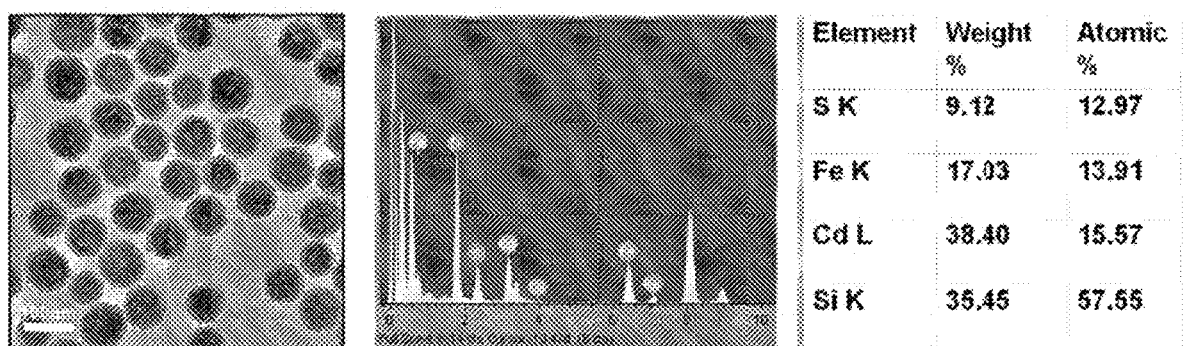
FIG. 8 shows TEM images and energy dispersive spectrum (EDS) of silica coated nanocrystal-$Fe_3O_4$ magneto-fluorescent multifunctional nanoparticles.
Figure 9A:
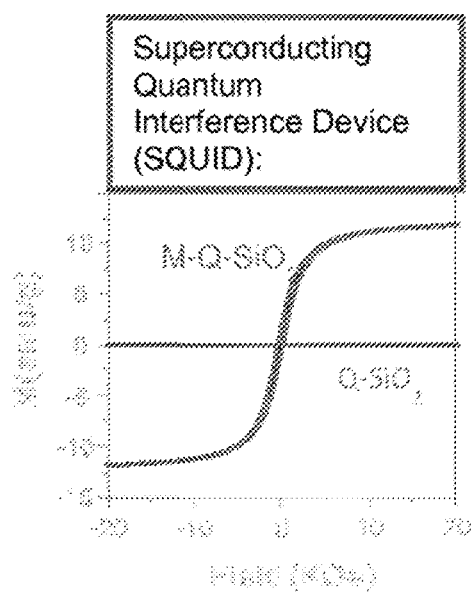
FIG. 9(a) shows results of magnetic measurements of semiconductor nanocrystal-only silica coated multifunctional nanoparticles (Q-$SiO_2$) and silica coated nanocrystal-$Fe_3O_4$ magneto-fluorescent multifunctional nanoparticles (M-Q-$SiO_2$); left, SQUID results; right, MRI results.
Figure 9A:
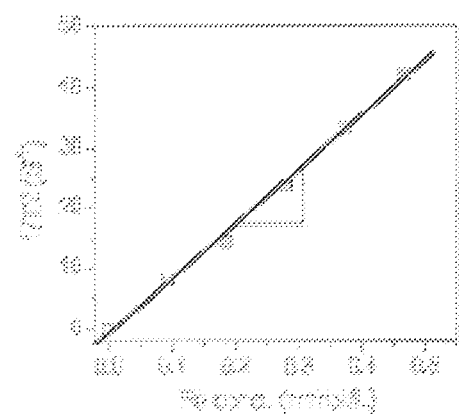
Figure 9A:
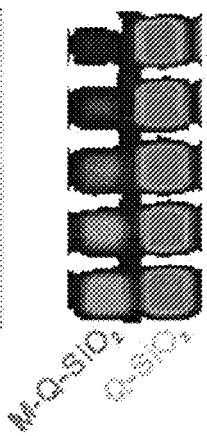
Figure 9B:
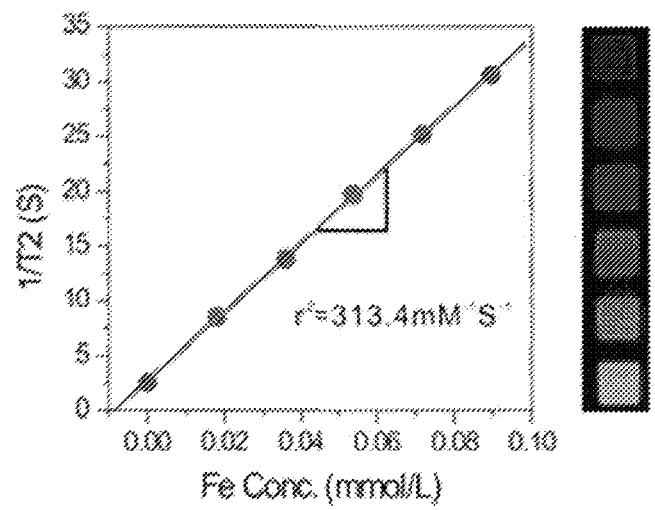
FIG. 9(b) shows in vitro magnetic resonance images (MRI) of assembled particles.

TEM images showed that each assembled multifunctional nanoparticle was uniformly coated with a thin silica shell (~10 nm thickness). EDS measurement showed that these particles indeed contained Si (FIG. 8).

Magnetic measurements (SQUID and MRI) confirmed that the magnetic properties of Fe$_3$O$_4$ nanoparticles remained intact after assembly into silica coated multifunctional nanoparticles (FIG. 9 (a)). FIG. 9(b) shows in vitro MRI of assembled particles and r$^2$ can reach as high as 313.4 mM$^{-1}$S$^{-1}$.

Figure 10:
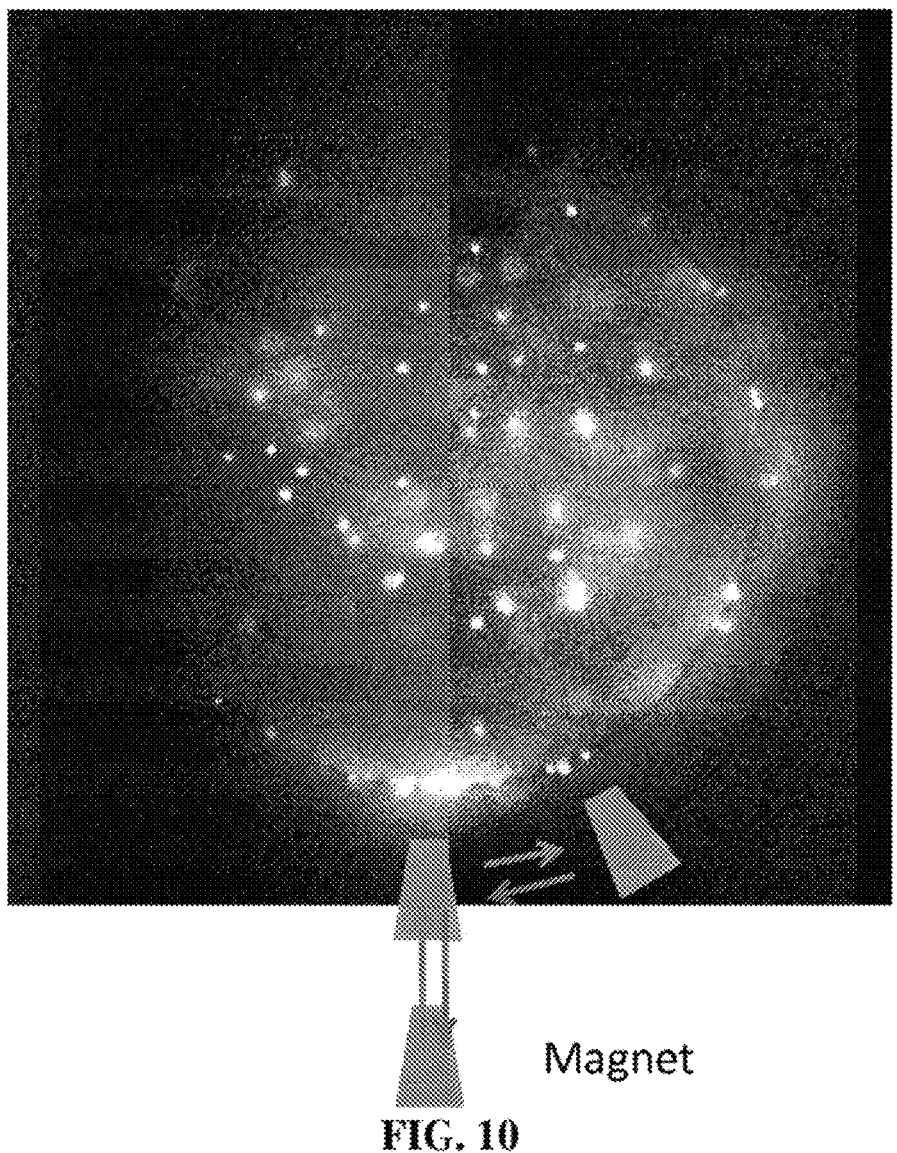
FIG. 10 shows a fluorescence microscope image of magneto-fluorescent multifunctional nanoparticles in a water droplet.

As shown in FIG. 10, silica coated magneto-fluorescent multifunctional nanoparticles were suspended in a water droplet. While in suspension, the multifunctional nanoparticles could be visually tracked using fluorescence microscopy, and manipulated magnetically: the multifunctional nanoparticles moved within the water droplet in response to a magnetic field.

Silica coated multifunctional nanoparticles were further derivatized. In one example, a silica coated multifunctional nanoparticle was functionalized with a poly(ethylene glycol) (PEG), by reaction with a suitable PEG silane. One suitable PEG silane is:

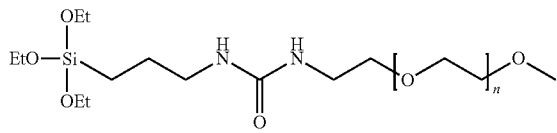

Such PEGylated silica coated multifunctional nanoparticles can have enhanced biocompatibility.

Figure 11:
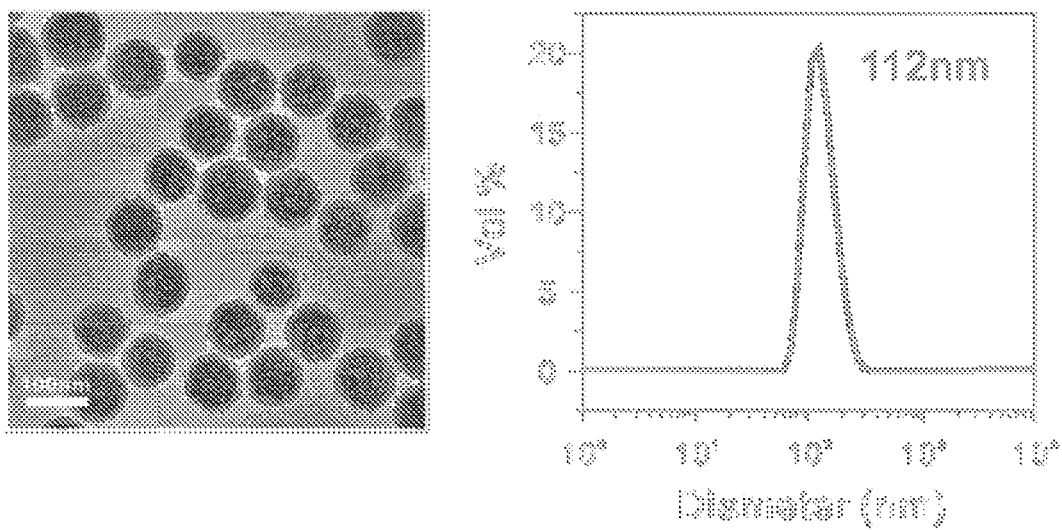
FIG. 11 shows a TEM image of PEGylated silica coated multifunctional nanoparticles (left) and diameter measurements of same (right).
Figure 12:
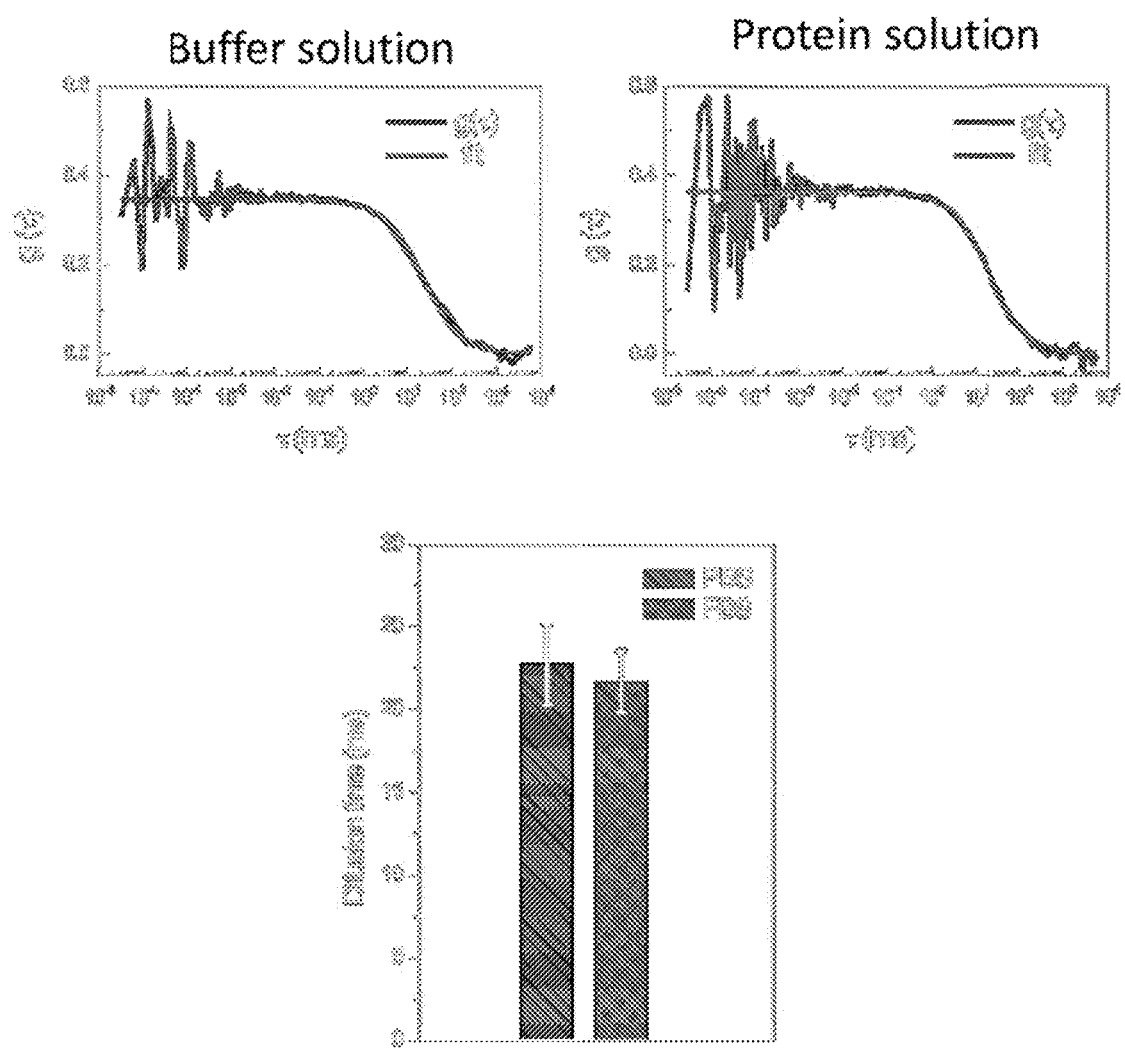
FIG. 12 shows results of fluorescence correlation spectroscopy of PEGylated silica coated multifunctional nanoparticles.

PEGylated silica coated multifunctional nanoparticles were found to have a diameter of 112 nm (FIG. 11). After incubation at 37° C. for four hrs., fluorescence correlation spectroscopy showed no change in hydrodynamic diameter, which indicated that the PEGylated nanoparticles did not undergo nonspecific protein binding (FIG. 12).

Figure 13:
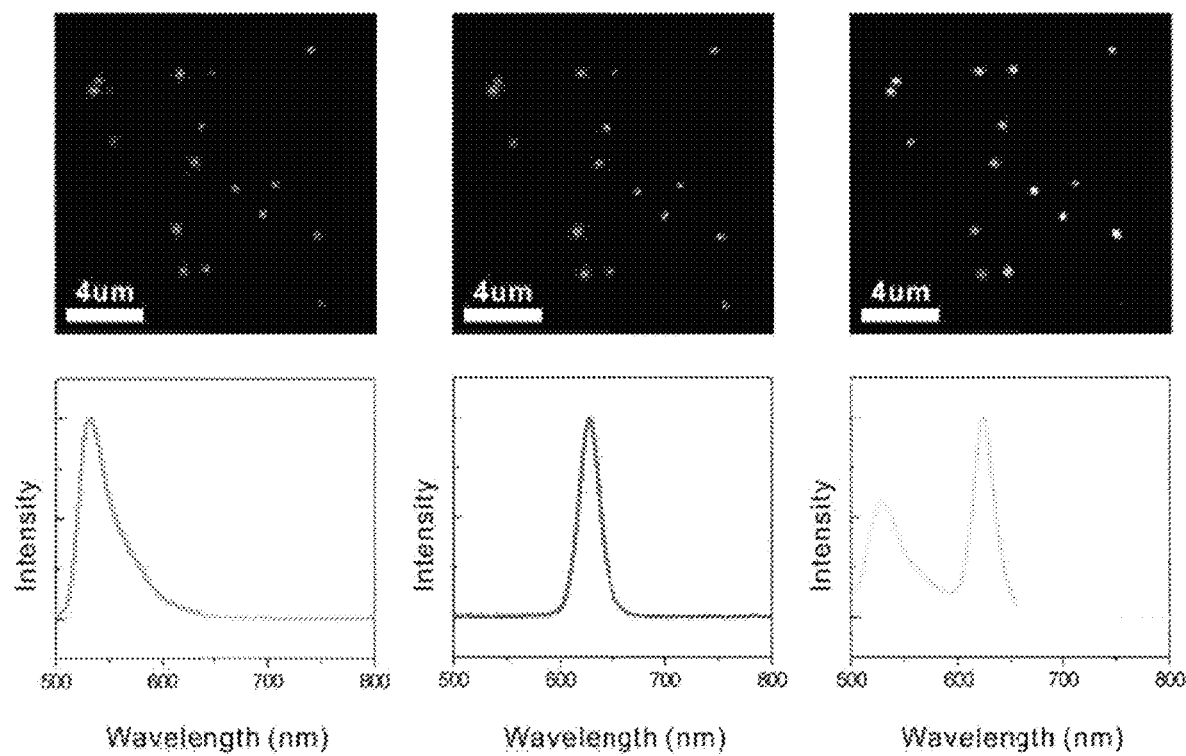
FIG. 13 shows fluorescence microscopy images (top) and fluorescence spectra (bottom) of silica coated multifunctional nanoparticles surface-modified with an organic dye.

In one example, a silica coated multifunctional nanoparticle was functionalized with (3-aminopropyl)trimethoxysilane (APTMS), affording the nanoparticle with surface accessible reactive amino groups. Those reactive amino groups can be a site for further functionalization of the nanoparticle. For example, FITC dye was attached to the nanoparticle via reaction with the reactive amino groups. FIG. 13 shows that these surface-modified silica coated multifunctional nanoparticles were consistently fluorescent both from the FITC dye (shown by the 525/50 band pass spectrum, left) and nanocrystals (600 long pass spectrum, middle) individually, and with a 500 long pass filter (right), the multifunctional nanoparticles showed simultaneous fluorescence from both FITC and nanocrystals.

Figure 14:
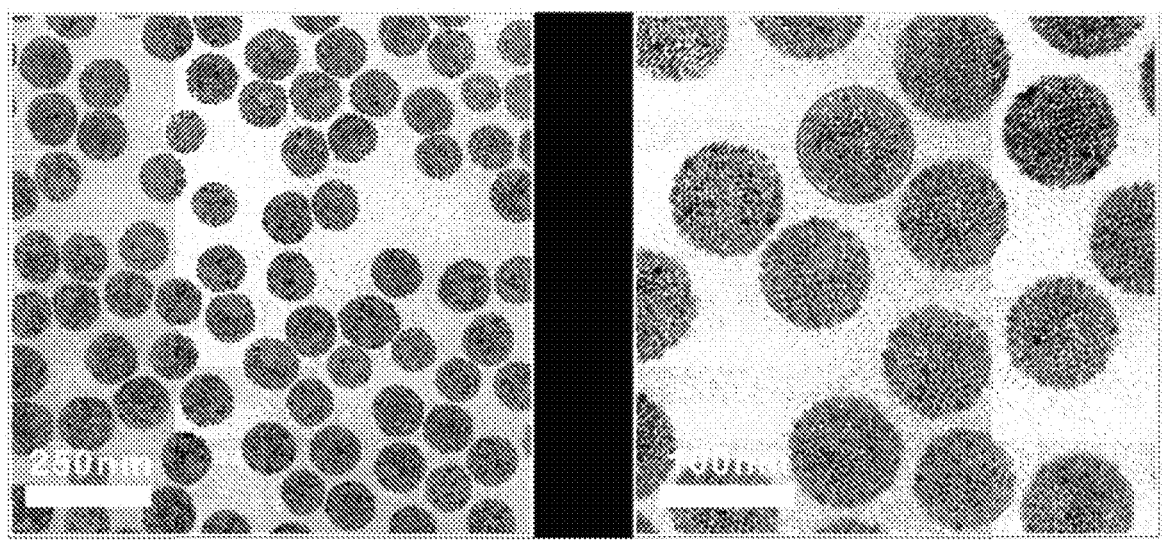
FIG. 14 shows TEM images of magneto-fluorescent multifunctional nanoparticles having a heterogeneous internal structure.
Figure 15:
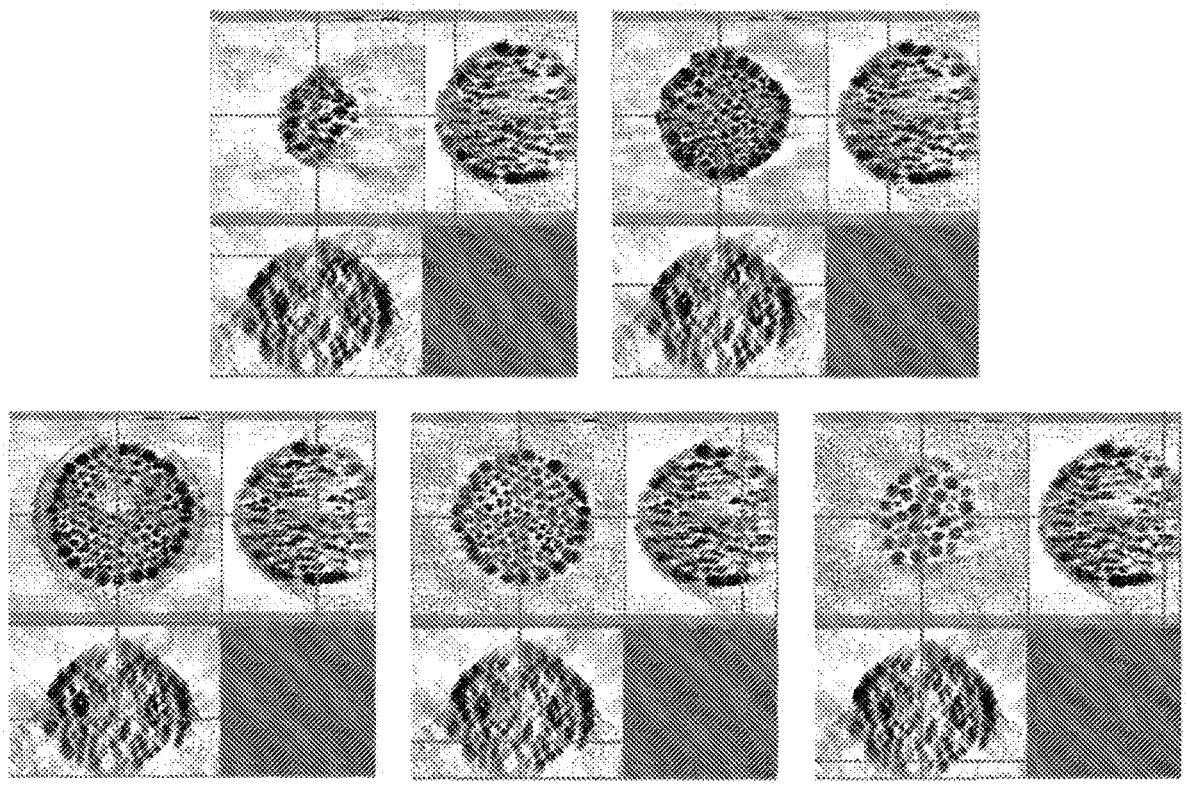
FIG. 15 shows TEM images of magneto-fluorescent multifunctional nanoparticles having a heterogeneous internal structure.

Internal structure of the multifunctional nanoparticles was also controlled. FIG. 14 shows TEM images of magneto-fluorescent multifunctional nanoparticles in which magnetic Fe$_3$O$_4$ nanoparticles were grouped toward the center of the multifunctional nanoparticle while semiconductor nanocrystals were grouped toward the periphery of the multifunctional nanoparticle. The makeup of constituent nanoparticles in the center and periphery was confirmed by EDS. FIG. 15.

Figure 16:
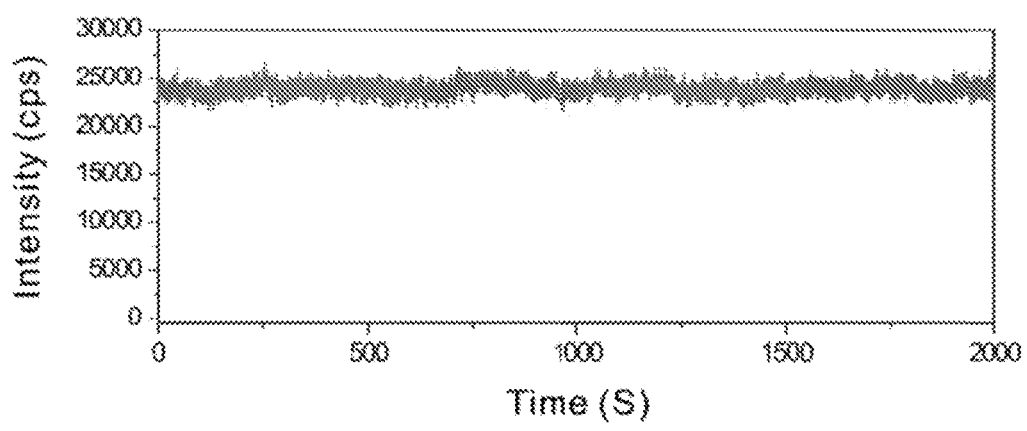
FIG. 16 shows that single multifunctional assembled particle is not "blinking" under laser excitation with an excitation power of 22 W/$cm^2$.

Photoluminescence (PL) Intensity Trace Measurement for Single Assembled Particle The silica-coated assembled particle in water solution was spun cast onto glass coverslips (Electron Microscopy Sciences). Individual particles were studied by confocal fluorescence microscopy using an oil immersion microscope objective (100×, 1.40 NA, Plan Apochromat). The SCSAPs were excited with a continuous wave laser at 532 nm with a power density of 22 W/cm$^2$. PL intensity time traces were recorded using pulse counters (National Instruments) and a correlator card (Timeharp 200, PicoQuant). All measurements were performed at room temperature. FIG. 16 shows that single multifunctional assembled particle is not "blinking" under laser excitation with a excitation power of 22 W/cm$^2$.

Intracellular Magnetic Manipulation of the Multifunctional Assembled Particles

Figure 17:
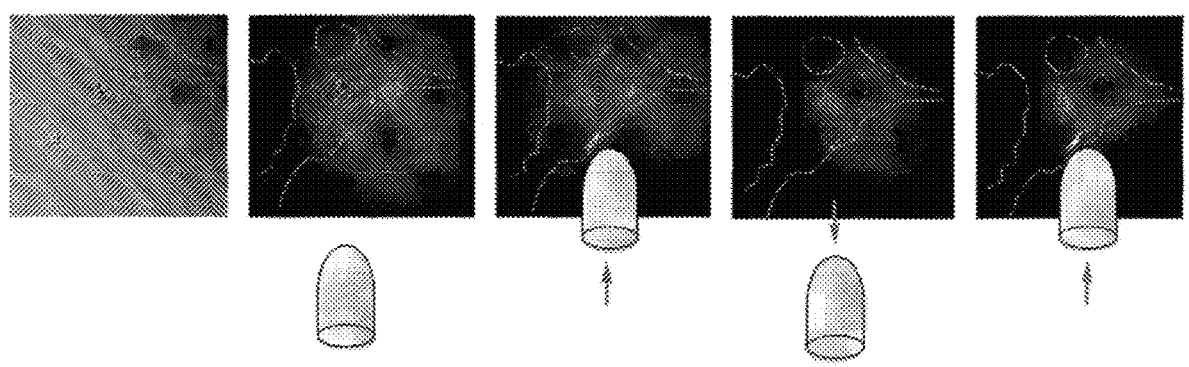
FIG. 17 shows intracellular manipulation of magneto-fluorescent multifunctional assembled particles.

PEGylated silica-coated assembled particles were observed with a wide field Olympus IX70 inverted microscope, equipped with a 100×, 1.45 NA objective, and coupled to a 488 nm laser line in an epifluorescence configuration. The emitted light was filtered out from the excitation laser by a dichroic filter with a 495 nm cut off and a band-pass emission filter centered at 605 nm, before being collected on a QUANTEM 512SC EMCCD camera (Photometrics). The particles were injected into living HeLa cell using a microinjector system (Femtojet, Eppendorf) and home-made micropipettes of 1 µm tip, pulled from borosilicates capillaries using the P-97 puller (Sutter Instrument). Particles were magnetically manipulated inside the cell using a simple magnetic tweezer made from a paramagnetic tip put on top of a small permanent magnet of Neodymium Iron Boron whose shape was a parallelepiped of 4×1×0.5 mm (supermagnet). FIG. 17 shows that PEGylated silica-coated multifunctional assembled particles can be manipulated inside living cell by external magnetic tweezer and simultaneously tracked using fluorescence microscopy.

In Vivo Multiphoton Imaging

200 µL PEGylated silica-coated multifunctional assembled particles were intravenous injected in mice bearing MCa IV breast metastasis brain tumor model. Multiphoton imaging was carried out on a custom-built multiphoton laser-scanning microscope using confocal laser-scanning microscope body (Olympus 300; Optical Analysis Corp.) and a broadband femtosecond laser source (High Performance MaiTai, Spectra-Physics). Image slices were taken at different time points (Pre-injection, 4 hours post-injection and 24 hours post-injection). Imaging studies were performed with a 20× magnification, 0.95NA water immersion objective (Olympus XLUMPlanFl, 1-UB965, Optical Analysis). Image analysis was carried out using ImageJ.

MRI experiments were performed on a 9.4 Tesla magnet (Magnex Scientific Ltd, Oxford, UK) equipped with a 60 mm inner diameter gradient coil (Resonance Research, Billerica, Mass.) and interfaced with a Bruker MRI console (Bruker Biospin, Billerica, Mass.). The gradient coil has a maximum strength of 1500 mT/m and a rise time of 100 ms. Images were acquired using a home built mouse headbirdcage coil. Mice were positioned on a custom made mouse cradle and anesthetized with 1.5% isoflurane in 50/50 $O_2$/medical air mixture with total flow rate of 1200 ml/min. Contrast agent injections were performed using an intravenous tail vein catheter.

T2-weighted Rapid Acquisition with Refocused Echoes (RARE) images were acquired with the following acquisition parameters: TE=10, RARE factor=8, TR=2500 ms, NA=4, 15 image slices, 0.5 mm slice thickness, 125 mm in-plane resolution. Tumor volume was determined from the T2 hyperintense tumor region of the brain.

Figure 18A:
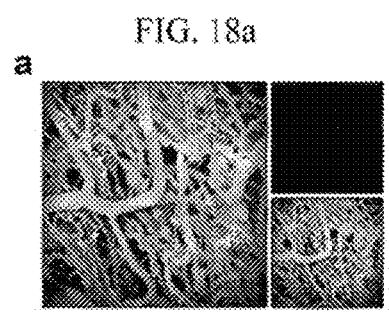
FIGS. 18a-f show in vivo dual modal imaging using magneto-fluorescence assembled particles.
Figure 18B:
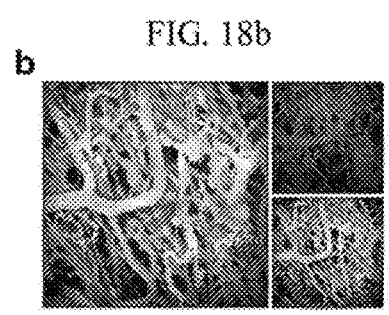
Figure 18C:
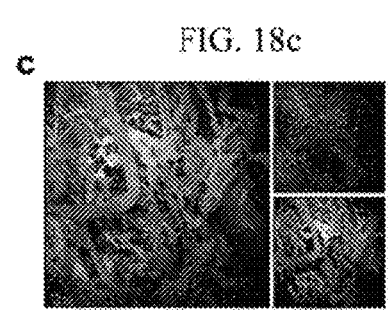
Figure 18D:
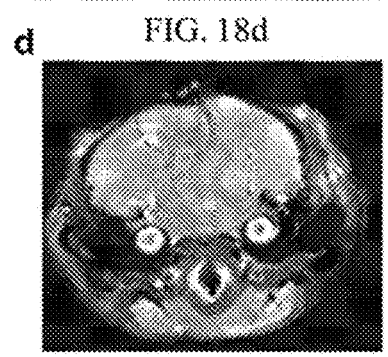
Figure 18E:
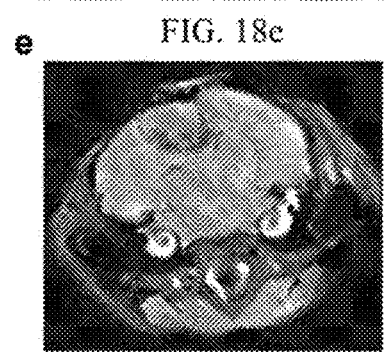
Figure 18F:
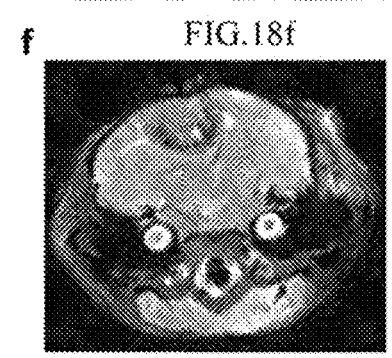

FIGS. 18a-18c show in vivo two-photon images and FIGS. 18d-18f show magnetic resonance images (MRI) of PEGylated silica-coated magneto-fluorescence multifunctional assembled particles that are systematically injected into brain tumor mice model. FIG. 18a and FIG. 18d show images of pre-injection. FIG. 18b and FIG. 18e show images after 4 hours of injection. FIG. 18c and FIG. 18f show images after 24 hours of injection. In FIGS. 18a-18c, small panels on the right side of each image show the multifunctional particles' signal in red channel (top) and blood vessel tracer (FITC-Dextran) signal in green channel (bottom). In FIGS. 18d-18f, dash lines indicate the tumor area in brain.

REFERENCES

Each of the following references is incorporated by reference in its entirety.
(1) Alivisatos, A. P. J. Phys. Chem. 1996, 100, 13226.
(2) Alivisatos, A. P. Science 1996, 271, 933.
(3) Murray, C. B.; Norris, D. J.; Bawendi, M. G. J. Am. Chem. Soc. 1993, 115, 8706.
(4) Chen, O.; Chen. X.; Yang, Y.; Lynch, J.; Wu, H.; Zhuang, J.; Cao, Y. C. Angew. Chem., Int. Ed. 2008, 47, 8683.
(5) Talapin, D. V.; Haubold, S.; Rogach, A. L.; Kornowski, A.; Haase, M.; Weller, H. J. Phys. Chem. B. 2001, 105, 2260.
(6) Insin, N.; Tracy, J. B.; Lee, H.; Zimmer, J. P.; Westervelt, R. M.; Bawendi, M. G. ACS Nano 2008, 2, 197.
(7) Ruan, G.; Vieira, G.; Henighan, T.; Chen, A.; Thakur, D.; Sooryakumar, R.; Winter, J. O. Nano Lett. 2010, 10, 2220.
(8) Yi, D. K.; Selvan, S. T.; Lee, S. S.; Papaefthymiou, G. C.; Kundaliya, D.; Ying, J. Y. J. Am. Chem. Soc. 2005, 127, 4990.
(9) Kim, B.; Taton, T. A. Langmuir 2007, 23, 2198.
(10) Hyeon, T. et al. J. Am. Chem. Soc. 128, 688 (2006).
(11) Cheon, J. et al. Angew. Chem. Int. Ed. 46, 86160 (2006).
(12) Winter, J. et al. Nano Lett. 10, 2220 (2010).
(13) Ying, J. et al. J. Am. Chem. Soc. 127, 4990 (2005).
(14) Insin, N. et al. ACS Nano. 2, 197 (2008).
(15) Han et al., Nature Biotech. 19, 2001, 631-635.
(16) U.S. Pat. No. 7,229,690.

Other embodiments are within the scope of the following claims.

What is claimed is:

1. A method of making a multifunctional nanoparticle, comprising:
    forming a mixture including a first solvent, a second solvent which is substantially immiscible with the first solvent, a first population of nanoparticles with a first property, and a surfactant,
    removing at least a portion of the first solvent from the mixture,
    adding an assembly polymer to the mixture, thereby associating the assembly polymer with the first population of nanoparticles to form a multifunctional nanoparticle including the first population of nanoparticles and the assembly polymer,
    adding a second population of nanoparticles with a second property, wherein the second property is different from the first property, the first population of nanoparticles and the second population of nanoparticles having a photoluminescence at different desired wavelengths, and
    adding an assembly polymer to the mixture, thereby associating the assembly polymer with the first population of nanoparticles and the second population of nanoparticles such that the first population of nanoparticles and the second population of nanoparticles are substantially evenly distributed and impart a combination of properties arising from the first and second populations in a single multifunctional nanoparticle.

2. The method of claim 1, wherein adding an assembly polymer includes contacting the mixture with a composition including the assembly polymer and a third solvent.

3. The method of claim 1, further comprising isolating the multifunctional nanoparticles from the mixture.

4. The method of claim 1, wherein the assembly polymer is selected to non-covalently associate with the first and second populations.

5. The method of claim 1, further comprising forming a shell including a silicon oxide on a surface of the multifunctional nanoparticle.

6. The method of claim 5, further comprising functionalizing the shell including a silicon oxide.

7. The method of claim 3, wherein functionalizing the shell including a silicon oxide includes covalently linking a dye, a polymer, a biomolecule, or a member of a binding pair to the metal oxide shell.

8. The method of claim 1, wherein the first population is a population of semiconductor nanocrystals.

9. The method of claim 1, wherein the second population is a population of semiconductor nanocrystals, magnetic nanoparticles, metal nanoparticles, carbon-based nanoparticles, polymer nanoparticles, or ceramic nanoparticles.

10. The method of claim 1, wherein the multifunctional nanoparticle has a diameter no greater than 1,000 nm.

11. The method of claim 1, wherein the multifunctional nanoparticle has a diameter no greater than 500 nm.

12. The method of claim 1, wherein the multifunctional nanoparticle has a diameter no greater than 100 nm.

13. The method of claim 1, wherein the first population has an average diameter no greater than 50 nm, and the second population has an average diameter no greater than 50 nm.

14. A method of studying a living organism comprising adding a multifunctional nanoparticle into the living organism, wherein the multifunctional nanoparticle includes
   a first population of nanoparticles with a first property,
   a second population of nanoparticles with a second property, wherein the second property is different from the first property, the first population of nanoparticles and the second population of nanoparticles having a photoluminescence at different desired wavelengths and
   an assembly polymer associated with the first population of nanoparticles and the second population of nanoparticles such that the first population of nanoparticles and the second population of nanoparticles are substantially evenly distributed and impart a combination of properties arising from the first and second populations in a single multifunctional nanoparticle.

15. The method of claim 14, wherein the living organism is a cell.

16. The method of claim 14, wherein the living organism is a mouse.

17. The method of claim 14, further comprising applying a magnetic field to the multifunctional nanoparticle.

18. The method of claim 14, wherein the multifunctional nanoparticle is both magnetic and photoluminescent.

19. The method of claim 14, wherein the multifunctional nanoparticle includes magnetic constituent nanoparticles and photoluminescent constituent nanoparticles.

* * * * *